(12) United States Patent
Rhee et al.

(10) Patent No.: US 8,734,476 B2
(45) Date of Patent: May 27, 2014

(54) COUPLING FOR SLIP RING ASSEMBLY AND ULTRASONIC TRANSDUCER IN SURGICAL INSTRUMENT

(75) Inventors: Sora Rhee, Cincinnati, OH (US); Samantha L. Sheets, West Chester, OH (US); Daniel J. Mumaw, Johannesburg (ZA); John A. Weed, III, Monroe, OH (US); Craig T. Davis, Cincinnati, OH (US); Scott A. Nield, Hamilton, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 13/272,614

(22) Filed: Oct. 13, 2011

(65) Prior Publication Data

US 2013/0096468 A1   Apr. 18, 2013

(51) Int. Cl.
*A61B 17/32*   (2006.01)

(52) U.S. Cl.
USPC ............................ 606/169; 606/170; 606/174

(58) Field of Classification Search
USPC .................................. 600/437–469; 601/1–3
See application file for complete search history.

(56) References Cited

U.S. PATENT DOCUMENTS

| | | | |
|---|---|---|---|
| 4,878,493 A | 11/1989 | Pasternak et al. |
| 5,107,155 A | 4/1992 | Yamaguchi |
| 5,277,694 A | 1/1994 | Leysieffer et al. |
| 5,322,055 A | 6/1994 | Davison |
| 5,449,370 A | 9/1995 | Vaitekunas |
| 5,630,420 A | 5/1997 | Vaitekunas |
| 5,800,336 A | 9/1998 | Ball et al. |
| 5,873,873 A | 2/1999 | Smith et al. |
| 5,935,144 A | 8/1999 | Estabrook |
| 5,938,633 A | 8/1999 | Beaupre |
| 5,944,737 A | 8/1999 | Tsonton et al. |
| 5,980,510 A | 11/1999 | Tsonton et al. |
| 6,051,010 A | 4/2000 | Dimatteo et al. |
| 6,325,811 B1 | 12/2001 | Messerly |
| 6,500,176 B1 | 12/2002 | Truckai et al. |
| 6,514,267 B2 | 2/2003 | Jewett |
| 6,520,185 B1 | 2/2003 | Bommannan et al. |
| 6,561,983 B2 | 5/2003 | Cronin et al. |
| 6,626,901 B1 | 9/2003 | Treat et al. |

(Continued)

FOREIGN PATENT DOCUMENTS

| | | |
|---|---|---|
| WO | WO 2009/046394 | 4/2009 |
| WO | WO 2009/070780 | 6/2009 |
| WO | WO 2009/073608 | 6/2009 |

OTHER PUBLICATIONS

U.S. Appl. No. 13/151,471, filed Jun. 2, 2011, Stulen.

(Continued)

*Primary Examiner* — Sanjay Cattungal
(74) *Attorney, Agent, or Firm* — Frost Brown Todd LLC

(57) ABSTRACT

An ultrasonic surgical instrument includes a body such as a handle assembly and an acoustic transmission assembly. The acoustic transmission assembly includes an ultrasonic transducer and an end effector. A mounting ring is positioned on a horn of the transducer. A rotatable drum is positioned distal to the mounting ring. Piezoelectric components of the transducer are positioned proximal to the mounting ring. Electrical conduits extend from the drum to the piezoelectric components and are routed over or through the mounting ring. The drum is coupled with a power source through a slip ring assembly to selectively activate the transducer.

20 Claims, 19 Drawing Sheets

(56) References Cited

U.S. PATENT DOCUMENTS

| | | |
|---|---|---|
| 6,666,875 B1 | 12/2003 | Sakurai et al. |
| 6,783,524 B2 | 8/2004 | Anderson et al. |
| 6,982,696 B1 | 1/2006 | Shahoian |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,292,227 B2 | 11/2007 | Fukumoto et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,416,101 B2 | 8/2008 | Shelton, IV et al. |
| 7,464,846 B2 | 12/2008 | Shelton, IV et al. |
| D594,983 S | 6/2009 | Price et al. |
| 7,583,564 B2 | 9/2009 | Ketahara et al. |
| 7,638,958 B2 | 12/2009 | Philipp et al. |
| 7,721,936 B2 * | 5/2010 | Shalton et al. ............. 227/180.1 |
| 7,738,971 B2 | 6/2010 | Swayze et al. |
| 7,846,155 B2 | 12/2010 | Houser et al. |
| 7,959,050 B2 | 6/2011 | Smith et al. |
| 8,011,551 B2 * | 9/2011 | Marczyk et al. ........... 227/175.1 |
| 8,210,411 B2 * | 7/2012 | Yates et al. ................ 227/175.1 |
| 2006/0079874 A1 | 4/2006 | Faller et al. |
| 2007/0016174 A1 * | 1/2007 | Millman et al. .................... 606/1 |
| 2007/0191713 A1 | 8/2007 | Eichmann et al. |
| 2007/0282333 A1 | 12/2007 | Fortson et al. |
| 2008/0057470 A1 * | 3/2008 | Levy et al. ..................... 433/118 |
| 2008/0167670 A1 * | 7/2008 | Shelton et al. ................ 606/167 |
| 2008/0200940 A1 | 8/2008 | Eichmann et al. |
| 2008/0221479 A1 * | 9/2008 | Ritchie et al. ................. 600/563 |
| 2008/0221491 A1 | 9/2008 | Slayton et al. |
| 2008/0228104 A1 | 9/2008 | Uber, III et al. |
| 2008/0255413 A1 | 10/2008 | Zemlok et al. |
| 2009/0030437 A1 * | 1/2009 | Houser et al. .................. 606/169 |
| 2009/0043797 A1 | 2/2009 | Dorie et al. |
| 2009/0099520 A1 * | 4/2009 | Millman et al. .............. 604/131 |
| 2009/0138006 A1 | 5/2009 | Bales et al. |
| 2009/0143797 A1 | 6/2009 | Smith et al. |
| 2009/0143798 A1 * | 6/2009 | Smith et al. .................... 606/169 |
| 2009/0143799 A1 * | 6/2009 | Smith et al. .................... 606/169 |
| 2009/0143800 A1 | 6/2009 | Deville et al. |
| 2009/0143801 A1 * | 6/2009 | Deville et al. .................. 606/169 |
| 2009/0143802 A1 * | 6/2009 | Deville et al. .................. 606/169 |
| 2009/0143803 A1 * | 6/2009 | Palmer et al. .................. 606/169 |
| 2009/0143804 A1 * | 6/2009 | Palmer et al. .................. 606/169 |
| 2009/0143805 A1 * | 6/2009 | Palmer et al. .................. 606/169 |
| 2009/0209979 A1 | 8/2009 | Yates et al. |
| 2009/0209990 A1 | 8/2009 | Yates et al. |
| 2010/0001036 A1 * | 1/2010 | Marczyk et al. ........... 227/175.1 |
| 2010/0069940 A1 | 3/2010 | Miller et al. |
| 2010/0076474 A1 * | 3/2010 | Yates et al. .................... 606/170 |
| 2010/0301095 A1 * | 12/2010 | Shelton et al. ............. 227/175.4 |
| 2011/0015660 A1 | 1/2011 | Wiener et al. |
| 2011/0087212 A1 | 4/2011 | Aldridge et al. |
| 2011/0087218 A1 | 4/2011 | Boudreaux et al. |
| 2011/0152901 A1 | 6/2011 | Woodruff et al. |
| 2011/0301579 A1 * | 12/2011 | Marczyk et al. .................... 606/1 |
| 2012/0116261 A1 * | 5/2012 | Mumaw et al. ..................... 601/2 |
| 2012/0179169 A1 * | 7/2012 | Swarup et al. ................ 606/130 |
| 2012/0265230 A1 * | 10/2012 | Yates et al. .................... 606/170 |
| 2012/0277663 A1 * | 11/2012 | Millman et al. ................. 604/26 |
| 2012/0292367 A1 * | 11/2012 | Morgan et al. ............. 227/175.1 |
| 2012/0296332 A1 * | 11/2012 | Chernov et al. ................. 606/45 |

OTHER PUBLICATIONS

U.S. Appl. No. 13/151,481, filed Jun. 2, 2011, Yates et al.
U.S. Appl. No. 13/151,488, filed Jun. 2, 2011, Shelton IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011, Felder et al.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux et al.
U.S. Appl. No. 13/270,667, filed Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
U.S. Appl. No. 13/274,480, filed Oct. 17, 2011, Mumaw et al.
U.S. Appl. No. 13/274,496, filed Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.
U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.

* cited by examiner

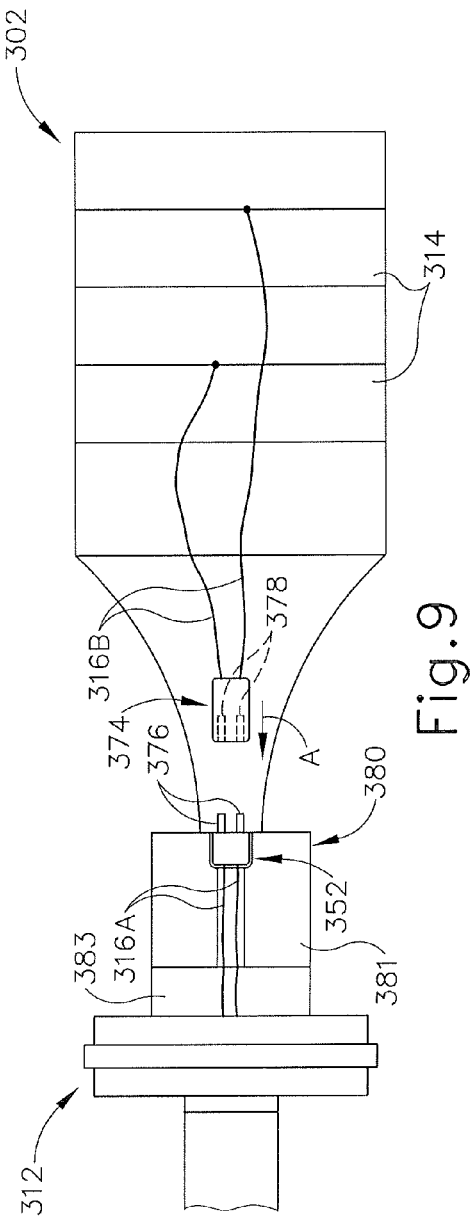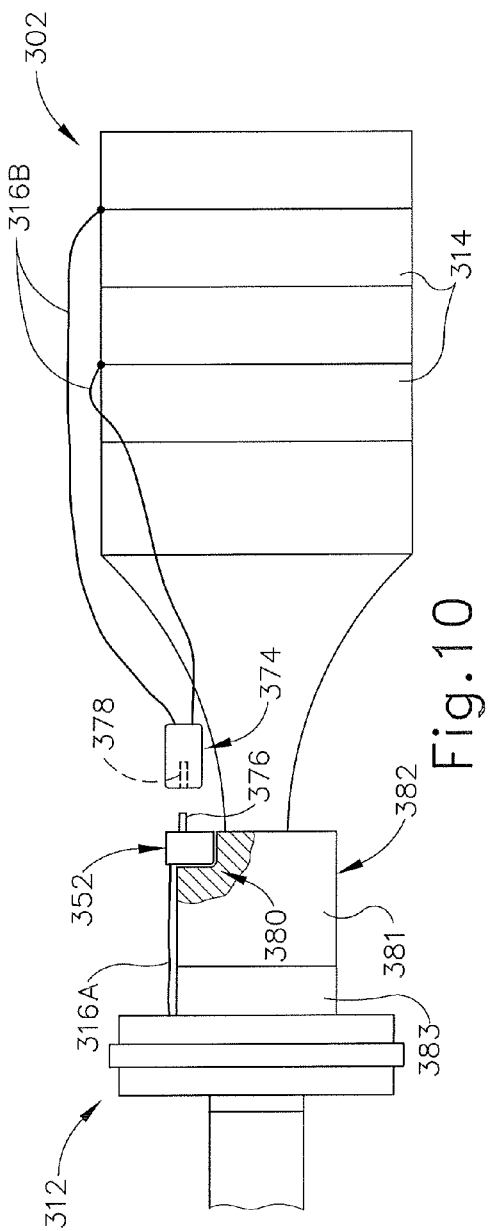

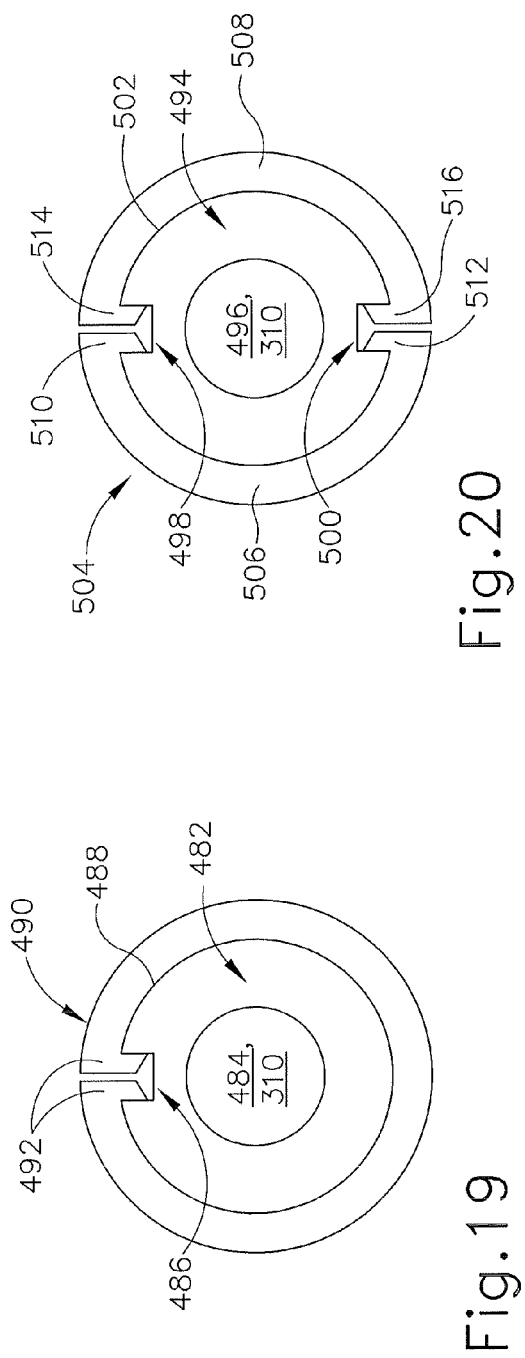
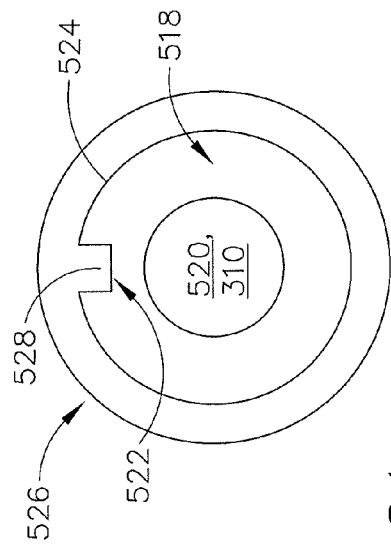
Fig.19  Fig.20  Fig.21

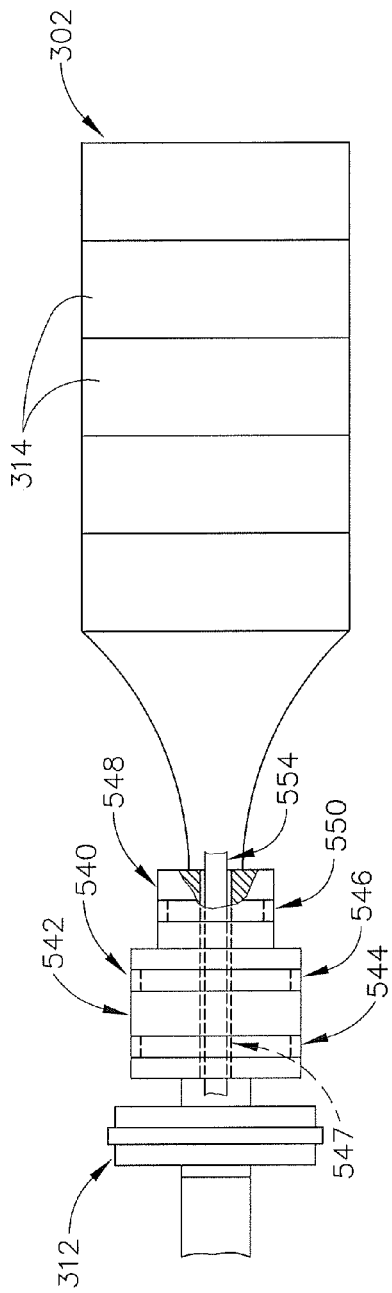
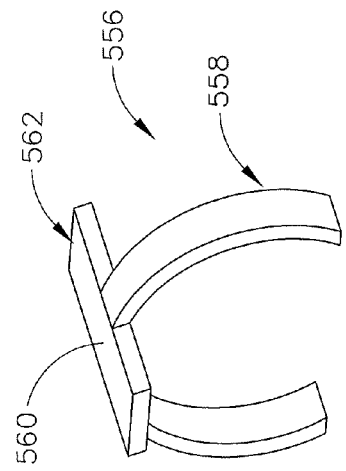
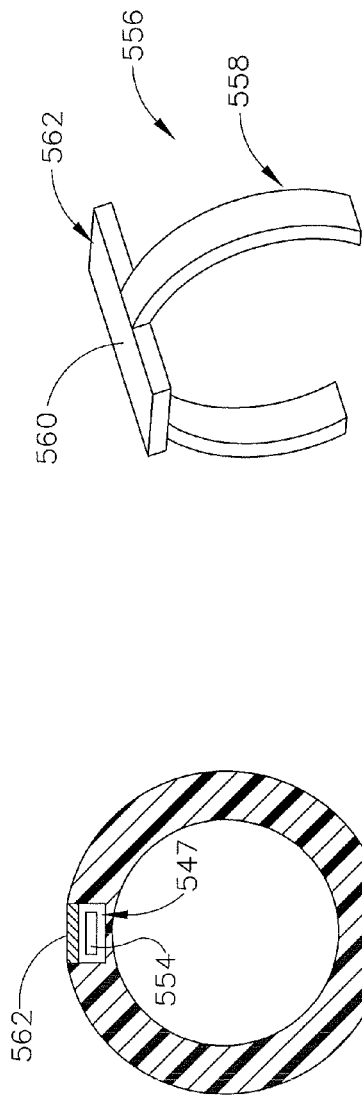

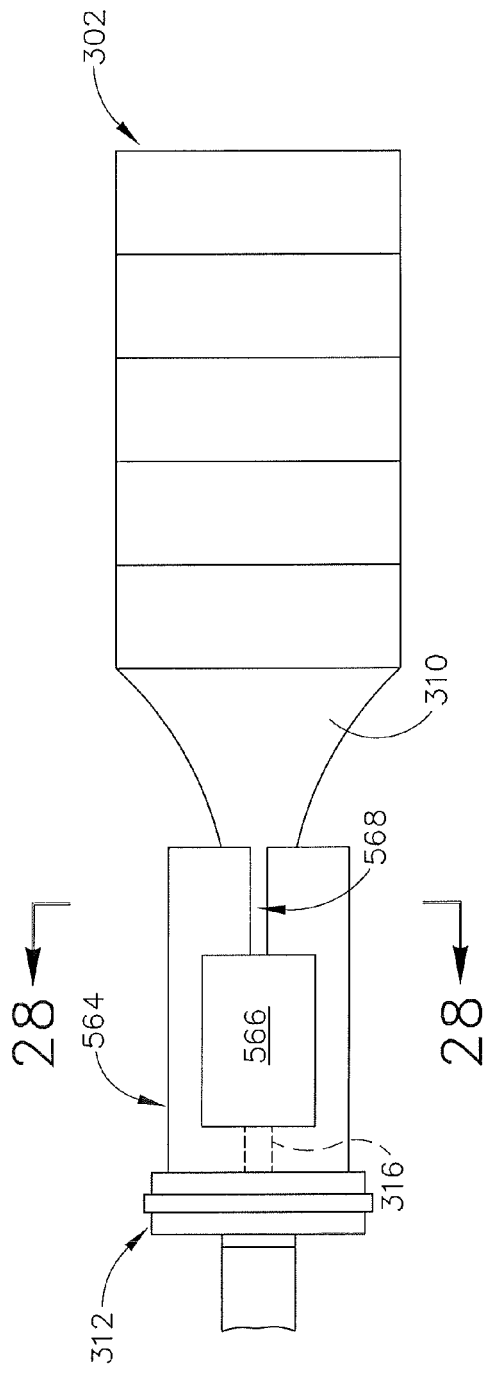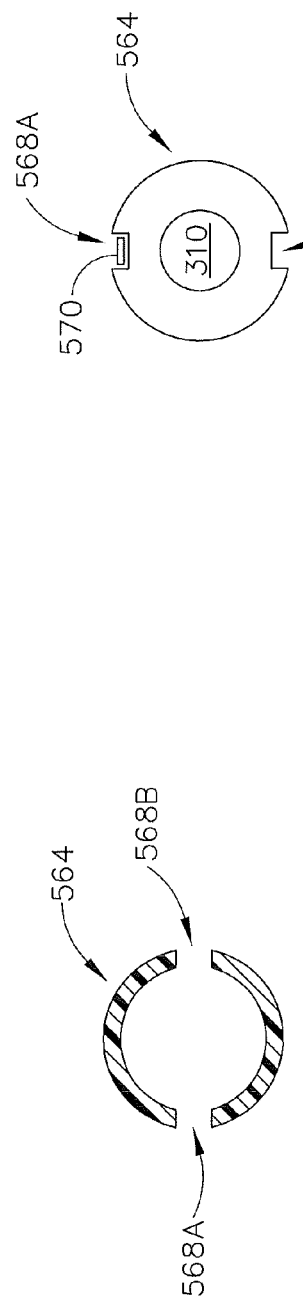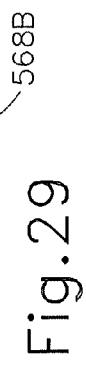

COUPLING FOR SLIP RING ASSEMBLY AND ULTRASONIC TRANSDUCER IN SURGICAL INSTRUMENT

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, the disclosure of which is incorporated by reference herein. Additionally, such surgical tools may include a cordless transducer such as that disclosed in U.S. Pat. Pub. No. 2009/0143797, entitled "Cordless Handheld Ultrasonic Cautery Cutting Device," published Jun. 4, 2009, the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9 depicts a plan view of an exemplary mounting ring within an exemplary rotatable assembly;

FIG. 10 depicts an elevation view of the rotatable assembly of FIG. 9;

FIG. 19 depicts an end view of an exemplary mounting ring and covering component assembly;

FIG. 20 depicts an end view of another exemplary mounting ring and covering component assembly where two portions of the covering component are each snap fitted into a pair of channels disposed in the mounting ring;

FIG. 21 depicts an end view of yet another exemplary mounting ring and covering component assembly where the covering component is a sleeve component snap fitted into a channel of the mounting ring;

FIG. 24 depicts an elevation view of an exemplary rotatable assembly including an exemplary mounting ring having exemplary annular channels disposed therein;

FIG. 25 depicts an end view showing o-rings disposed in the exemplary annular channels of FIG. 24;

FIG. 26 depicts a perspective view of an alternative exemplary retention clip;

FIG. 27 depicts a fragmentary elevation view of an exemplary rotatable assembly including an exemplary mounting ring with an exemplary cap feature;

FIG. 28 depicts a cross-sectional view of the exemplary mounting ring of FIG. 27 taken along line 28-28 of FIG. 27;

FIG. 29 depicts an end view of the exemplary mounting ring of FIG. 27;

Figure 1:
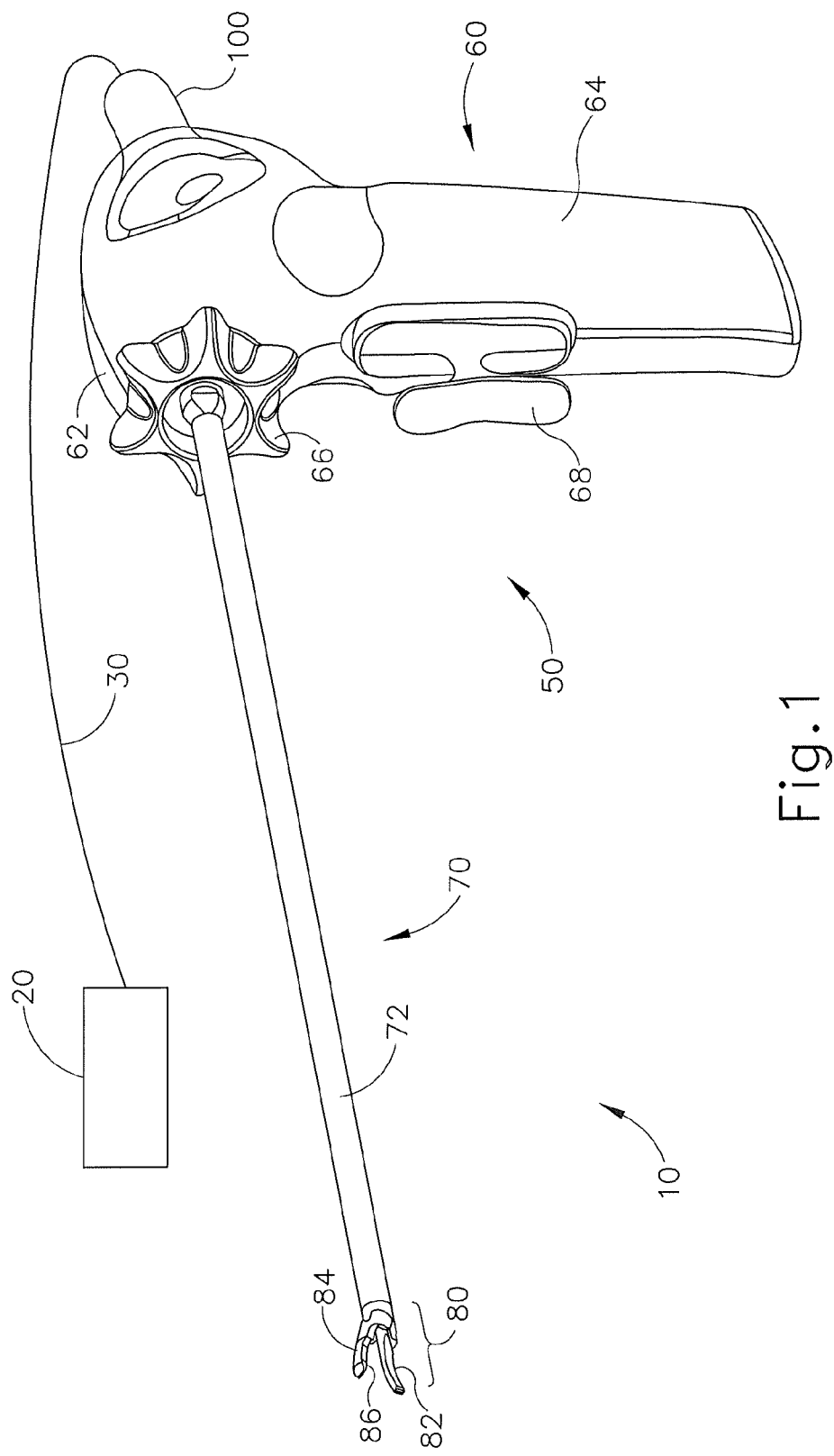
FIG. 1 depicts a perspective view of an exemplary surgical system comprising a surgical instrument and a generator.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Ultrasonic Surgical System

FIG. 1 shows an exemplary ultrasonic surgical system (10) comprising an ultrasonic surgical instrument (50), a generator (20), and a cable (30) coupling generator (20) to surgical instrument (50). In some versions, generator (20) comprises a GEN 300 sold by Ethicon Endo-Surgery, Inc. of Cincinnati, Ohio. By way of example only, generator (20) may be constructed in accordance with the teachings of U.S. Pub. No. 2011/0087212, entitled "Surgical Generator for Ultrasonic and Electrosurgical Devices," published Apr. 14, 2011, the disclosure of which is incorporated by reference herein. While surgical instrument (50) is described herein as an ultrasonic surgical instrument, it should be understood that the teachings herein may be readily applied to a variety of surgical instruments, including but not limited to endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation, such as that disclosed in U.S. Pat. Pub. No. 2009/0143797, entitled "Cordless Hand-held Ultrasonic Cautery Cutting Device," published Jun. 4, 2009, the disclosure of which is incorporated by reference herein. For instance, surgical device (50) may include an integral and portable power source such as a battery, etc. Furthermore, surgical device (50) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example, transmission assembly (70) is configured as an elongated, thin tubular assembly for endoscopic use, but it should be understood that transmission assembly (70) may alternatively be a short assembly, such as those disclosed in U.S. Pat. Pub. No. 2007/0282333, entitled "Ultrasonic Waveguide and Blade," published Dec. 6, 2007, and U.S. Pat. Pub. No. 2008/0200940, entitled "Ultrasonic Device for Cutting and Coagulating," published Aug. 21, 2008, the disclosures of which are incorporated by reference herein. Transmission assembly (70) of the present example comprises an outer sheath (72), an inner tubular actuating member (not shown), a waveguide (not shown), and an end effector (80) located on the distal end of transmission assembly (70). In the present example, end effector (80) comprises a blade (82) that is mechanically and acoustically coupled to the waveguide, a clamp arm (84) operable to pivot at the proximal end of transmission assembly (70), and a clamp pad (86) coupled to clamp arm (84). It should also be understood that clamp arm (84) and associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein.

Exemplary versions of end effector (80) and transmission assembly (70) will be discussed in greater detail below in reference to the example shown in FIG. 4. In some versions, transducer (100) comprises a plurality of piezoelectric elements (not shown) that are compressed between first resonator (not shown) and second resonator (not shown) to form a stack of piezoelectric elements. The piezoelectric elements may be fabricated from any suitable material, for example, lead zirconate-titanate, lead meta-niobate, lead titanate, and/or any suitable piezoelectric crystal material, for example. Transducer (100) further comprises electrodes, including at least one positive electrode and at least one negative electrode that are configured to create a voltage potential across the one or more piezoelectric elements, such that the piezoelectric elements convert the electrical power into ultrasonic vibrations. The ultrasonic vibrations are transmitted to blade (82) via the waveguide in transmission assembly (70).

Multi-piece handle assembly (60) of the present example comprises a mating housing portion (62) and a lower portion (64). Mating housing portion (62) is configured to receive transducer (100) at a proximal end of mating housing portion

(62) and to receive the proximal end of transmission assembly (70) at a distal end of mating housing portion (62). A rotation knob (66) is shown in the present example to rotate transmission assembly (70) and transducer (100), but it should be understood that rotation knob (66) is merely optional. Mating housing portion (62) will be discussed in greater detail below in reference to FIG. 2. Lower portion (64) of multi-piece handle assembly (60) shown in FIG. 1 includes a trigger (68) and is configured to be grasped by a user using a single hand. One merely exemplary alternative version for lower portion (64) is depicted in FIG. 1 of U.S. Pat. Pub. No. 2011/0015660, entitled "Rotating Transducer Mount for Ultrasonic Surgical Instruments," published Jan. 20, 2011, the disclosure of which is incorporated by reference herein. Toggle buttons (69), shown in FIG. 2 of the present disclosure, are located on a distal surface of lower portion (64) and are operable to selectively activate transducer (100) at different operational levels using generator (20). For instance, a first toggle button (69) may activate transducer (100) at a maximum energy level while a second toggle button (69) may activate transducer (100) at a minimum, non-zero energy level. Of course, toggle buttons (69) may be configured for energy levels other than a maximum and/or minimum energy level as will be apparent to one of ordinary skill in the art in view of the teachings herein. Moreover, the toggle buttons may be located anywhere else on multi-piece handle assembly (60), on transducer (100), and/or remote from surgical instrument (50), and any number of toggle buttons may be provided.

While multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as a separate trigger portion (operable either by a user's hand or foot) and a separate mating housing portion (62). Such a trigger portion may be operable to activate transducer (100) and may be remote from mating housing portion (62). Multi-piece handle assembly (60) may be constructed from a durable plastic (such as polycarbonate or a liquid crystal polymer), ceramics, metals, and/or any other suitable material as will be apparent to one of ordinary skill in the art in view of the teachings herein. Other configurations for multi-piece handle assembly (60) will also be apparent to those of ordinary skill in the art in view of the teachings herein.

Further still, surgical instrument (50) may be constructed in accordance with at least some of the teachings of U.S. Pat. No. 5,322,055 entitled "Clamp Coagulator/Cutting System for Ultrasonic Surgical Instruments," issued Jun. 21, 1994, the disclosure of which is incorporated by reference herein; U.S. Pat. No. 5,873,873 entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811 entitled "Blades with Functional Balance Asymmetries for use with Ultrasonic Surgical Instruments," issued Dec. 4, 2001, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pub. No. 2009/0143797, entitled "Cordless Hand-held Ultrasonic Cautery Cutting Device," published Jun. 4, 2009, the disclosure of which is incorporated by reference herein; U.S. Pub. No. 2010/0069940 entitled "Ultrasonic Device for Fingertip Control," published Mar. 18, 2010, the disclosure of which is incorporated by reference herein; U.S. Pub. No. 2011/0015660, entitled "Rotating Transducer Mount for Ultrasonic Surgical Instruments," published Jan. 20, 2011, the disclosure of which is incorporated by reference herein; and/or U.S. Provisional Application Ser. No. 61/410,603, filed Nov. 5, 2010, entitled "Energy-Based Surgical Instruments," the disclosure of which is incorporated by reference herein.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

II. Exemplary Coupling Assemblies for Ultrasonic Surgical Instrument

In some instances it may be useful to detach transmission assembly (70) from multi-piece handle assembly (60) and transducer (100). For instance, a detachable transmission assembly (70) may permit the reuse of multi-piece handle assembly (60) with multiple transmission assemblies (70) having various end effectors (80). By way of example only, the various end effectors (80) may have different sized and/or shaped blades (82) or the various end effectors (80) may have entirely different functions, such as RF end effectors, stapling end effectors, cutting end effectors, etc. Furthermore, a single multi-piece handle assembly (60) may be reused for different operations by a user by removing a dirty transmission assembly (70), optionally cleaning multi-piece handle assembly (60), and coupling a new transmission assembly (70) to multi-piece handle assembly (60) for a new operation. Accordingly, configuring multi-piece handle assembly (60) to couple with a variety of transmission assemblies (70) may be preferable for some users of surgical instrument (50).

A. Exemplary Multi-Piece Handle Assembly

Figure 2:
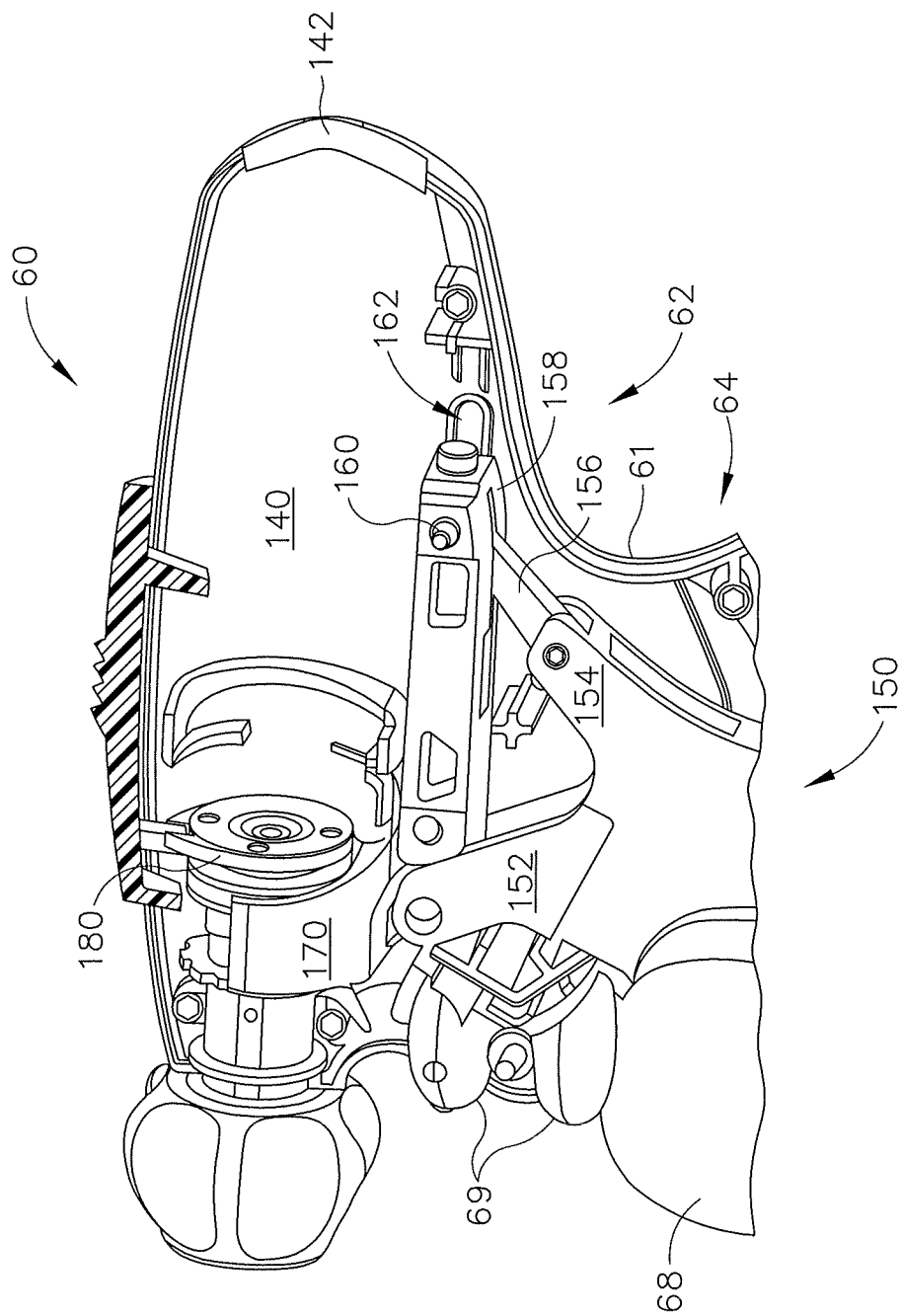
FIG. 2 depicts a partial side elevation view of an exemplary surgical instrument with a portion of a cover removed to show the interior of a mating housing portion of an exemplary multi-piece handle assembly.

FIG. 2 shows a partial side view of multi-piece handle assembly (60) with a portion of a cover (61) removed to show the internal components contained within mating housing portion (62) and a section of lower portion (64). As described above, lower portion (64) includes a pivotable trigger (68) and a pair of toggle buttons (69). Trigger (68) of the present example is pivotable from a distal, open position to a proximal, closed position. A trigger assembly (150) is coupled to trigger (68) and is pivotally supported within multi-piece handle assembly (60). Trigger assembly (150) of the present example comprises a pivotable attachment arm (152) that may be pivoted about a pin (not shown), a trigger arm (154), an intermediate link (156), and an actuation arm (158). Actuation arm (158) is coupled to a trigger yoke (170) at the distal end of actuation arm (158). Actuation arm (158) comprises one or more mounting pins (160) extending outwardly from actuation arm (158) and pins (160) are sized to be slidably received in corresponding elongated channel (162) formed in cover (61). Accordingly, when trigger (68) is pivoted proximally from the open position to the closed position attachment arm (152) and trigger arm (154) pivot within multi-piece handle assembly (60). Intermediate link (156) coupled to trigger arm (154) transfers this pivoting motion from trigger arm (154) to actuation arm (158) to slidably translate actuation arm (158) proximally via pins (160) within channel (162). Trigger yoke (170), which is coupled to actuation arm (158), is translated proximally as well. In the present example, trigger yoke (170) is coupled to a force-limiting mechanism (180), which is further coupled to transmission assembly (70) as will be described in more detail below, to operate inner tubular actuating member (74). A cavity (140), shown in FIG. 2, is configured to receive transducer (100) therein from a transducer aperture (142) formed in cover (61). Cavity (140) is configured to receive at least a portion of transducer (100) therein such that transducer (100) and transmission assembly (70) may be coupled together. Still other configurations for multi-piece handle assembly (60) will be apparent to one of ordinary skill in the art in view of the teachings herein.

B. Exemplary Transducer

Figure 3:
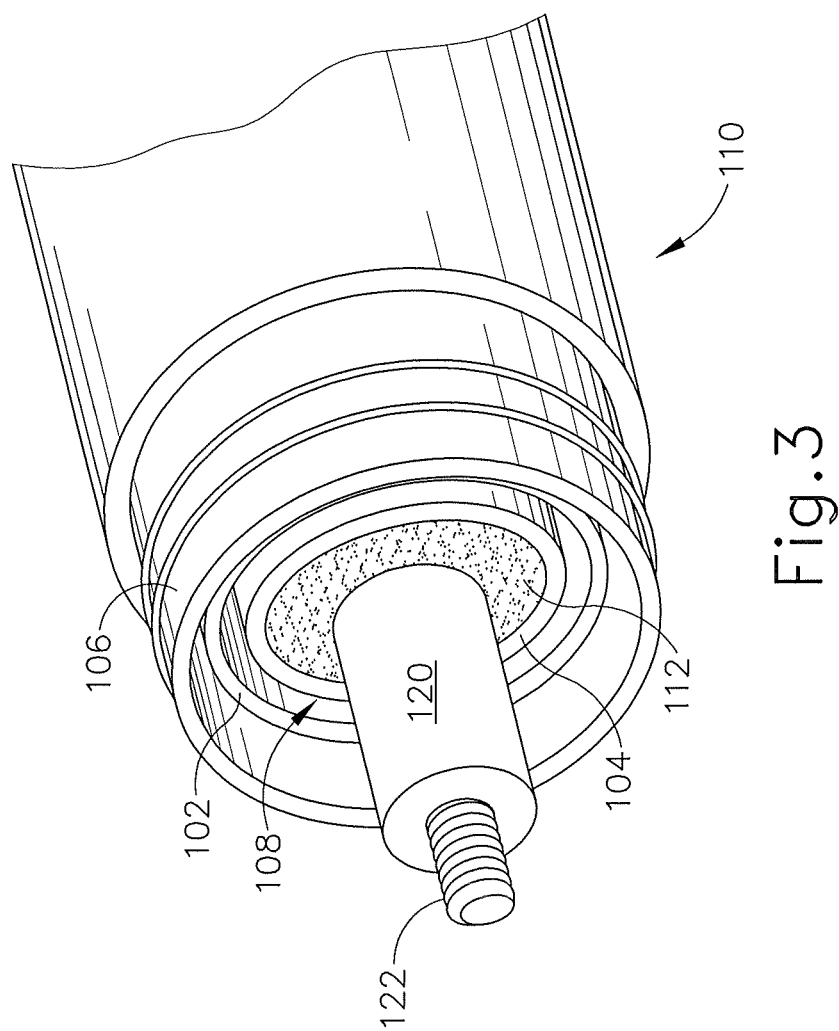
FIG. 3 depicts a partial perspective view of a distal end of an exemplary transducer.

As shown in FIG. 3, transducer (100) of the present example is a tubular component that is coupled to generator (20) via cable (30), though it should be understood that transducer (100) may instead be a cordless transducer. For instance, transducer (100) may instead receive power from a power source that is contained within handle assembly (60), in accordance with the teachings of various references cited herein or otherwise. In the present example, transducer (100) includes a first conductive ring (102) and a second conductive ring (104), which are disposed within a body (110) of transducer (100). In the present example, first conductive ring (102) comprises a ring member having one or more electrical contacts that are disposed on the ring member and that are configured to electrically couple first conductive ring (102) to a power source. First conductive ring (102) is disposed between body (110) and a horn (120) extending distally from body (110). Horn (120) comprises distal horn threads (122) such that horn (120) is coupleable to waveguide (210), as will be discussed below in reference to FIG. 4. First conductive ring (102) of the present example is coaxial with and adjacent to a flange (106). Flange (106) of the present example is configured to further mechanically couple transducer (100) within multi-piece handle assembly (60). A transducer cavity (108) is disposed between first conductive ring (102) and a second conductive ring (104) such that first conductive ring (102) is electrically isolated from second conductive ring (104) and/or other conductive components of transducer (100). First conductive ring (102) is located on a non-conductive platform extending distally from body (110). First conductive ring (102) is electrically coupled to cable (30), shown in FIG. 1, by one or more electrical wires or conductive etchings (not shown) within body (110). Such electrical coupling of first conductive ring (102) to cable (30) may include a slip ring to facilitate free rotation of transducer (100) relative to cable (30).

Second conductive ring (104) of transducer (100) similarly comprises a ring member that is disposed between body (110) and horn (120). Second conductive ring (104) is disposed between first conductive ring (102) and horn (120). As is shown in FIG. 3, first and second conductive rings (102, 104) are coaxial members. Second conductive ring (104) is likewise electrically isolated from first conductive ring (102) and other conductive components of transducer (100). Similar to first conductive ring (102), second conductive ring (104) extends from the non-conductive platform. One or more washer-shaped spacers (112) may be disposed between second conductive ring (104) and horn (120) to isolate the vibrations transmitted through horn (120) from the other components of transducer (100). Second conductive ring (104) is also electrically coupled to cable (30), shown in FIG. 1, by one or more electrical wires or conductive etchings (not shown) within body (110). Such electrical coupling of second conductive ring (104) to cable (30) may also include a slip ring to facilitate free rotation of transducer (100) relative to cable (30). One merely exemplary suitable ultrasonic transducer (100) is Model No. HP054, sold by Ethicon Endo-Surgery, Inc. of Cincinnati, Ohio, though it should be understood that any other suitable transducer may be used.

As shown in the present example, the distal end of transducer (100) threadably couples to the proximal end of a transmission assembly via horn (120). The distal end of transducer (100) also interfaces with one or more electrical conduits (not shown) via first and second conductive rings (102, 104) to electrically couple transducer (100) to toggle buttons (69) to provide a user with finger-activated controls for activating transducer (100) while using surgical instrument (50). The interface between the one or more electrical conduits and the first and second conductive rings (102, 104) may include a slip ring connection to permit free rotation of transducer (100) relative to multi-piece handle assembly (60). Still other configurations for transducer (100) will be apparent to one of ordinary skill in the art in view of the teachings herein. For instance, first and second conductive rings (102, 104) may be omitted from the distal end of transducer (100) and the electrical coupling of transducer (100) to toggle buttons (69) may be accomplished by alternative structures, such as conductors at the proximal end of transducer (100), conductors located along the side of body (110) of transducer (100), directly from cable (30), and/or otherwise. When transducer (100) of the present example is activated via a toggle button (69), transducer (100) is operable to create mechanical energy in the form of linear oscillations or vibrations, at an ultrasonic frequency (such as 55.5 kHz). When transducer (100) is coupled to transmission assembly (70) via horn (120), these mechanical oscillations are transmitted through the internal waveguide of transmission assembly (70) to end effector (80). In the present example, with blade (82) being coupled to the waveguide, blade (82) thereby oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to also cauterize the tissue. While some configurations for transmission assembly (70) and transducer (100) have been described, still other suitable configurations for transmission assembly (70) and transducer (100) will be apparent to one of ordinary skill in the art in view of the teachings herein.

C. Exemplary Transmission Assembly for Threaded Attachment

As noted previously, in some instances it may be useful to detach transmission assembly (70) from multi-piece handle assembly (60) and transducer (100). Merely exemplary instances include the use of multi-piece handle assembly (60) with multiple transmission assemblies (70) having different sized and/or shaped blades (82), use with various end effectors (80) with entirely different functions and/or modalities (e.g., RF end effectors, stapling end effectors, cutting end effectors, etc.), or for reuse of a single multi-piece handle assembly (60) for multiple operations by a user. Accordingly, a version permitting the user to swap transmission assemblies (70) with multi-piece handle assembly (60) may be useful.

Figure 4:
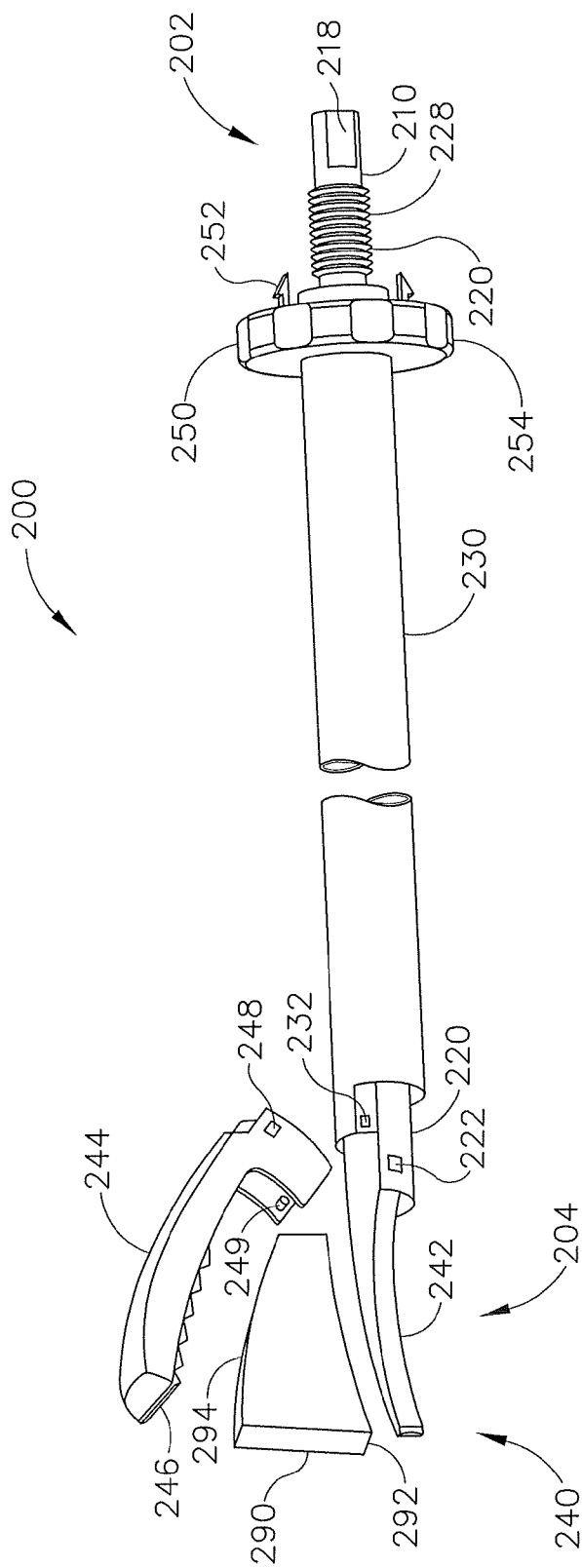
FIG. 4 depicts a perspective view of an exemplary transmission assembly.

One merely exemplary transmission assembly (200) is shown in FIG. 4 having a proximal end (202), a distal end (204), a waveguide (210), an inner tubular actuating member (220), an outer sheath (230), and an end effector (240) at the distal end of transmission assembly (200). In the present example, waveguide (210), inner tubular actuating member (220), and outer sheath (230) are coaxial members with waveguide (210) in the center, inner actuating member (220) disposed about waveguide (210), and outer sheath (230) disposed about inner actuating member (220).

Referring to distal end (204) of transmission assembly (200) first, end effector (240) comprises a blade (242), a clamp arm (244), and one or more optional clamp pads (246). In the present example, blade (242) is coupled to waveguide (210) such that the mechanical vibrations transmitted to waveguide (210) from transducer (100) are also transmitted to blade (242). Merely exemplary couplings for blade (242) to waveguide (210) include welding blade (242) to waveguide (210), integrally forming blade (242) with waveguide (210), mechanically or chemically coupling blade (242) to waveguide (210), and/or any other suitable configuration as will be apparent to one of ordinary skill in the art in view of the teachings herein. In some versions, blade (242) is a curved blade, such as blade (242) shown in FIG. 4; and in some versions blade (242) may be a straight blade. Furthermore, blade (242) may have a variety of shapes and sizes. In the present example, blade (242) is a tapered rectangular blade, though it should be understood that blade (242) may be cylindrical, triangular, hemi-cylindrical, square, hooked, and/or any other shape for blade (242). Furthermore, additional features may be added to blade (242), including spherical tips, hooked tips, square tips, serrated edging, and/or any other additional features. Still other configurations for blade (242) will be apparent to those of ordinary skill in the art in view of the teachings herein.

Clamp arm (244) of the present example is a curved member that corresponds to the curvature of blade (242). Clamp arm (244) may optionally include clamp pads (246) to grip or secure tissue against blade (242). Such clamp pads may be configured in accordance with at least some of the teachings of U.S. Pat. Pub. No. 2006/0079874, entitled "Tissue Pad Use with an Ultrasonic Surgical Instrument," published Apr. 13, 2006. Pivotal movement of clamp arm (244) with respect to blade (242) is accomplished by a first pair of pivot points (248) on clamp arm (244) that pivotally couple to outer sheath (230) and a second set of pivot points (249) on clamp arm (244) that pivotally couple to inner tubular actuating member (220). In the present example, outer sheath (230) is coupleable to multi-piece handle assembly (60) through a rotation knob (250), thereby grounding outer sheath (230). First set of pivot points (248) of clamp arm (244) are pivotally connected to outer sheath (230) via corresponding through holes (232) on outer sheath (230). In some versions, first set of pivot points (248) comprise through holes and a securing pin or rivet may be inserted through first set of pivot points (248) and through through holes (232) to secure clamp arm (244) to outer sheath (230). The pin in this version may be laser welded to clamp arm (244) or the pin may be laser welded to outer sheath (230). Of course through holes (232) may instead be outwardly extending pins and first set of pivot points (248) may be through holes. Still other configurations for first set of pivot points (248) and through holes (232) will be apparent to one of ordinary skill in the art in view of the teachings herein.

Second set of pivot points (249) of clamp arm (244) are pivotally connected to inner tubular actuating member (220) via corresponding through holes (222) on inner tubular actuating member (220). In some versions, second set of pivot points (249) comprise through holes and a securing pin or rivet may be inserted through second set of pivot points (249) and through through holes (222) to secure clamp arm (244) to inner tubular actuating member (220). The pin in this version may be laser welded to clamp arm (244) or the pin may be laser welded to inner tubular actuating member (220). Of course through holes (222) may instead be outwardly extending pins and second set of pivot points (249) may be through holes. Still other pivotable configurations for second set of pivot points (249) and through holes (222) will be apparent to one of ordinary skill in the art in view of the teachings herein.

With clamp arm (244) so secured to outer sheath (230) and inner tubular actuating member (220), clamp arm (244) is pivotable when inner tubular actuating member (220) translates longitudinally. In the present example, inner tubular actuating member (220) is translatable relative to the longitudinal axis of outer sheath (230) and is coupled to force-limiting mechanism (180) within multi-piece handle assembly (60). Thus, when force-limiting mechanism (180) translates via trigger (68) and trigger assembly (150), clamp arm (244) is pivotable from an open position to a closed position. It should be understood that, as with other components referred to herein, clamp arm (84, 244) is merely optional Likewise, trigger (68) and trigger assembly (150) and the components described herein for pivoting clamp arm (84, 244) are also merely optional. Thus, some versions of end effector (80, 240) may simply consist of a blade (82, 842) and/or other features.

As shown in FIG. 4, a spacer (290) is insertable between clamp arm (244) and blade (242) to maintain clamp arm (244) in the open position. Spacer (290) has a flat bottom surface (292) and an angled top surface (294) in this example. Top surface (294) is set at an angle to maintain clamp arm (244) in the open position relative to blade (242) when bottom surface (292) abuts blade (242). In some versions, bottom surface (292) may be configured to snap or clip onto blade (242) to secure spacer (290) relative to blade (242). Alternatively, a recess may be provided in spacer (290) such that spacer (290) may be slid onto blade (242). Further still, an adhesive may be applied to bottom surface (292) and/or top surface (294) to also secure spacer (290). Thus, when spacer (290) is inserted between clamp arm (244) and blade (242), clamp arm (244) is prevented from pivoting to a closed position. This may permit a user to couple transmission assembly (200) to multi-piece handle assembly (60) while maintaining both clamp arm (244) and trigger (68) in their respective open positions. Alternatively, a user may couple transmission assembly (200) to multi-piece handle assembly (60) without the use of spacer (290). For example, the user may couple different components of transmission assembly (200) with different components of handle assembly (60) at different times, such as in the manner described below or otherwise.

Referring now to proximal end (202) of transmission assembly (200), a rotation knob (250) couples outer sheath (230) to multi-piece handle assembly (60). In the present example, rotation knob (250) comprises an inner ring portion (not shown) having one or more connectors (252) extending proximally therefrom, an outer ring (254), and a pin (not shown) extending through outer ring (254), outer sheath (230), inner tubular actuating member (220), and waveguide (210). Accordingly, when outer ring (254) of rotation knob (250) is rotated, waveguide (210), inner tubular actuating member (220), and outer sheath (230) also rotate. Inner ring portion and outer ring (254) of the present example are complementary bearing components such that outer ring (254) is rotatable relative to inner ring portion. It should be understood that the pin does not extend though inner ring portion. As previously noted, inner ring portion includes connectors (252). In the present example connectors (252) are shown as snap-fit connectors, though other suitable connecting features, such as threading, adhesives, pins, clips, snaps, and/or other connectors may be used as will be apparent to one of ordinary skill in the art in view of the teachings herein. When transmission assembly (200) is assembled with multi-piece handle assembly (60) and transducer (100), as will be discussed below, connectors (252) of the present example insert into one or more recesses (not shown) and couple rotation knob (250) to cover (61) of multi-piece handle assembly (60). A release mechanism, such as a push button (not shown) on multi-piece handle assembly (60) or on rotation knob (250) may be provided to decouple connectors (252) from cover (61) when transmission assembly (200) is to be removed. Alternatively, connectors (252) may be designed to break-away when transmission assembly (200) is decoupled. Further still, if threading is used, inner portion of rotation knob (250) may be rotated to decouple from multi-piece handle assembly (60). Still other suitable configurations for rotation knob (250) will be apparent to one of ordinary skill in the art in view of the teachings herein.

Still referring to proximal end (202) of transmission assembly (200), external threads (228) are included at the proximal end of inner tubular actuating member (220) as shown in FIG. 4. External threads (228) screw into complementary threads (not shown) of force-limiting mechanism (180), which is in turn driven by trigger assembly (150). Additionally, a recess having internal threading (218) is included at the proximal end of waveguide (210) as shown in FIG. 4. Internal threading (218) screws onto horn threads (122) to mechanically and acoustically couple waveguide (210) to transducer (100). Of course other suitable configurations for transmission assembly (200) will be apparent to one or ordinary skill in the art in view of the teachings herein. Similarly, various other suitable ways in which transmission assembly (200) may be coupled with handle assembly (60) will be apparent to those of ordinary skill in the art in view of the teachings herein.

III. Exemplary Drum, Mounting Ring, and Transducer Assemblies

Examples described below relate to connections and uses of disposable acoustic transmission assemblies with reusable handle portions of ultrasonic surgical instruments. Additional exemplary modifications that may be provided for instrument (50) will be described in greater detail below. Various suitable ways in which the below teachings may be incorporated into instrument (50) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (50) or devices taught in the references cited herein. The below teachings may be readily applied to various other kinds of instruments, including instruments that would not be classified as ultrasonic surgical instruments. Various other suitable devices and settings in which the below teachings may be applied will be apparent to those of ordinary skill in the art in view of the teachings herein.

Figure 5:
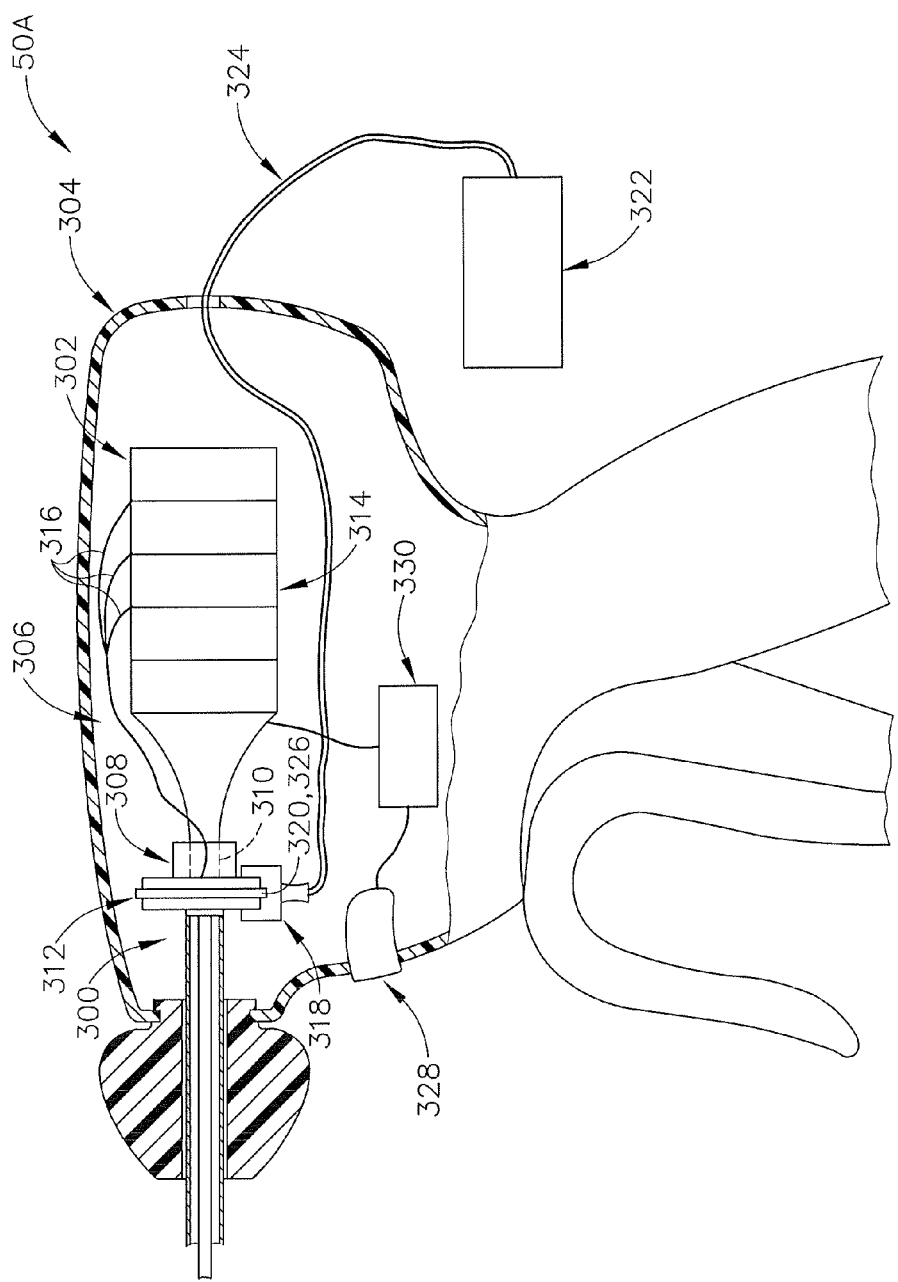
FIG. 5 depicts an elevation view of an exemplary surgical instrument showing a rotatable acoustic assembly.

Referring to FIG. 5, acoustic transmission assembly (300) is connected to transducer (302) within handpiece assembly (304) of instrument (50A) in a manner similar to that described above for connecting waveguide (210) of transmission assembly (70) to transducer (100). Acoustic transmission assembly (300) and transducer (302) together define an acoustic assembly (306). Mounting ring (308) is positioned on horn (310) of transducer (302). Mounting ring (308) structurally supports transducer (302) while permitting transducer (302) to rotate relative to handpiece assembly (304). A drum (312) is distally positioned with respect to mounting ring (308). Drum (312) is fixedly secured to transducer (302) such that drum (312) rotates with transducer (302) relative to handpiece assembly (304). Drum (312) also provides an electrical interface for transducer (302) as will be described in greater detail below. Piezoelectric elements (314) receive wires (316) on transducer (302) and are proximally positioned with respect to mounting ring (308).

Contact assembly (318) is fixed within handpiece assembly (304) of surgical instrument (50A). Contact assembly (318) is resiliently biased against outer circumference (320) of drum (312), such that electrical conduits around circumference (320) connect a stationary power supply to rotating transducer (302). One lead is for ground in a first electrical conduit, and another lead is for a high side voltage in a second electrical conduit with a separate contact assembly (318). For example, contact assembly (318) is electrically coupled to generator (322) by conduit (324), including one or more wires. Power from generator (322) is thereby transmitted to stationary contact assembly (318). Contact assembly (318) provides an electrical contact to a slip ring such as slip ring (326) disposed about rotatable drum (312). One or more wires (316) connected to drum (312) then transmit the received power to transducer (302). In use, mounting ring (308) is disposed between drum (312) and transducer (302), such that wires (316) must pass through our around mounting ring (308) in order to couple drum (312) with transducer (302). The versions of mounting ring assemblies disclosed below thus describe exemplary ways to pass wires (316) through or over a mounting ring. The mounting ring assemblies may be attached to horn (310) and may be configured to rotate with horn (310) within rotary bearings housed in handpiece assembly (304) of surgical instrument (50A). Alternatively, the mounting ring assemblies may be configured to house horn (310) and rotary bearings may be disposed between the mounting ring assemblies and horn (310) to allow horn (310) to rotate within a respective mounting ring assembly. Such bearings may be positioned such that they do not receive and/or transmit ultrasonic vibrations from horn (310).

Button (328) is in communication with controller (330) and is thereby operable to selectively activate acoustic assembly (306). In some versions, two or more buttons (328) are included. For instance, each button (328) may be operable to activate acoustic assembly (306) at a respective different power level. Acoustic transmission assembly (300), transducer (302) of acoustic assembly (306), and the associated mounting ring and drum assembly are rotatable as a unit to form a rotatable assembly in some versions. It should be understood that handpiece assembly (304) may have a variety of other components, features, and configurations. Some exemplary alternative components, features, and configurations are taught in various references cited herein; while other alternatives will be apparent to those of ordinary skill in the art in view of the teachings herein.

A. Exemplary Spiral Channel and Clip Assembly

Figure 6:
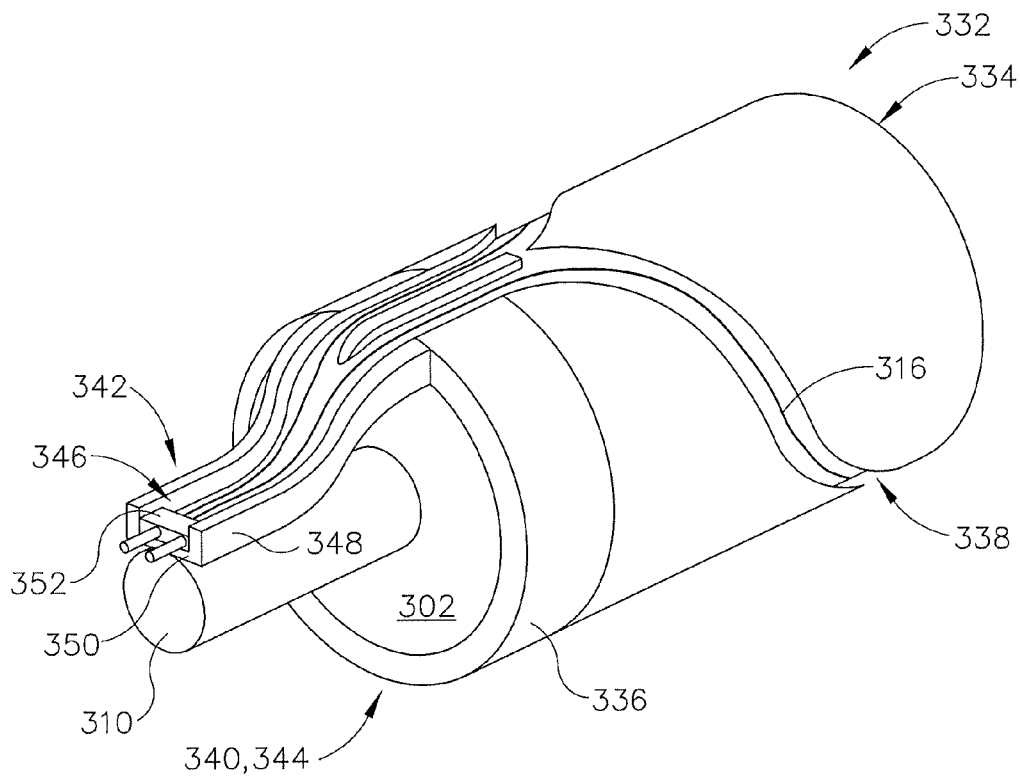
FIG. 6 depicts a perspective view of an exemplary transducer mounting assembly.
Figure 7:
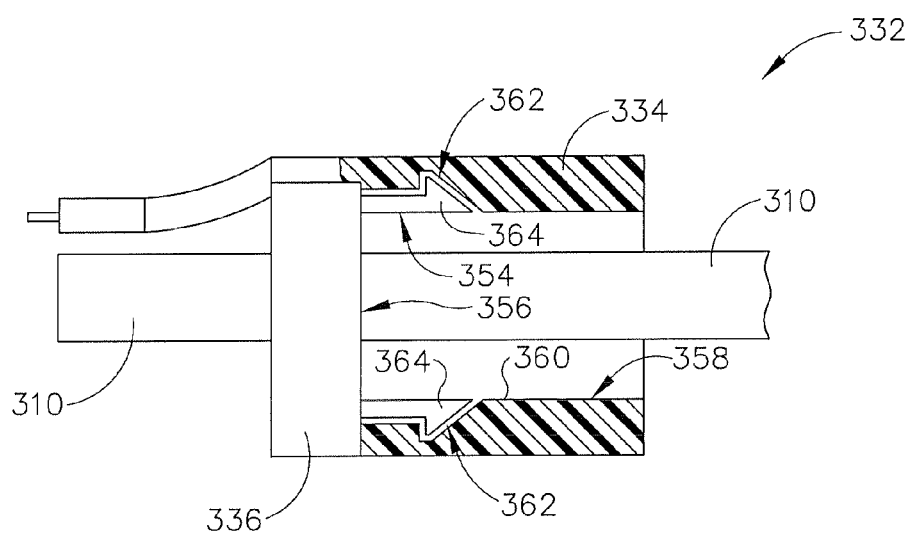
FIG. 7 depicts an elevation view of the assembly of FIG. 6.

FIGS. 6-7 show exemplary spiral channel and clip assembly (332) including mounting ring (334) and clip (336). Assembly (332) may be used as a variation of mounting ring (308) in instrument (50A). FIG. 6 shows mounting ring (334) including spiral channels (338) about an outer circumference. Spiral channels (338) are configured to retain wires (316). In use, mounting ring (334) is rotatable along with acoustic transmission assembly (300) and transducer (302). When wires (316) are retained in channels (338) of mounting ring (334), wires (316) rotate along with mounting ring (334) such that wires (316) do not interfere with the rotation of mounting ring (334) or any other component of the rotatable assembly. In particular, having wires (316) in channels (338) permits an annular bearing (not shown) to be disposed about the exterior of mounting ring (334), to structurally support mounting ring (334) and transducer (302) in an instrument body while permitting mounting ring (334) and transducer (302) to rotate relative to the instrument body, without the wires (316) being crimped or contacted by the annular bearing.

Clip (336) includes annular portion (340) and elongate connector housing portion (342) extending from proximal end (344) of annular portion (340). Elongate connector housing portion (342) includes pocket (346) defined by sidewalls (348) and retainer wall (350) disposed therebetween. Retainer wall (350) extends over horn (310) of transducer (302). Wires (316) connect to two-prong connector (352) disposed in pocket (346) of clip (336). Connector (352) is connectable to a mating connector (not shown) of transducer (302) to electrically connect wires (not shown) extending from a proximal end of transducer (302) to wires (316) extending through/along mounting ring (334). In this example, the other ends of wires (316) are coupled with a drum (e.g., drum (312), as described above), which is further coupled to a power source (e.g., generator (322), as described above) via a slip ring assembly (e.g., contact assembly (318), as described above). Wires (316) thus transmit power from the power source to transducer (302).

FIG. 7 shows prongs (354) extending from distal end (356) of clip (336). Mounting ring (334) includes interior aperture (358) configured to receive horn (310) and/or other portions of transducer (302). Interior walls (360) define aperture (358). Notches (362) are defined in interior walls (360). Notches (362) are configured to receive protrusions (364) of prongs (354) in a retaining connection, such as a press-fit connection or a snap-fit connection in which protrusions (364) are resiliently biased within notches (362). Alternatively, prongs (354) may include notches configured to be received in protrusions extending from interior walls (360) and which are resiliently biased against the notches in prongs (354). Other suitable ways in which clip (336) and mounting ring (334) may be coupled will be apparent to those of ordinary skill in the art in view of the teachings herein.

B. Exemplary Clamshell Assembly

Figure 8:
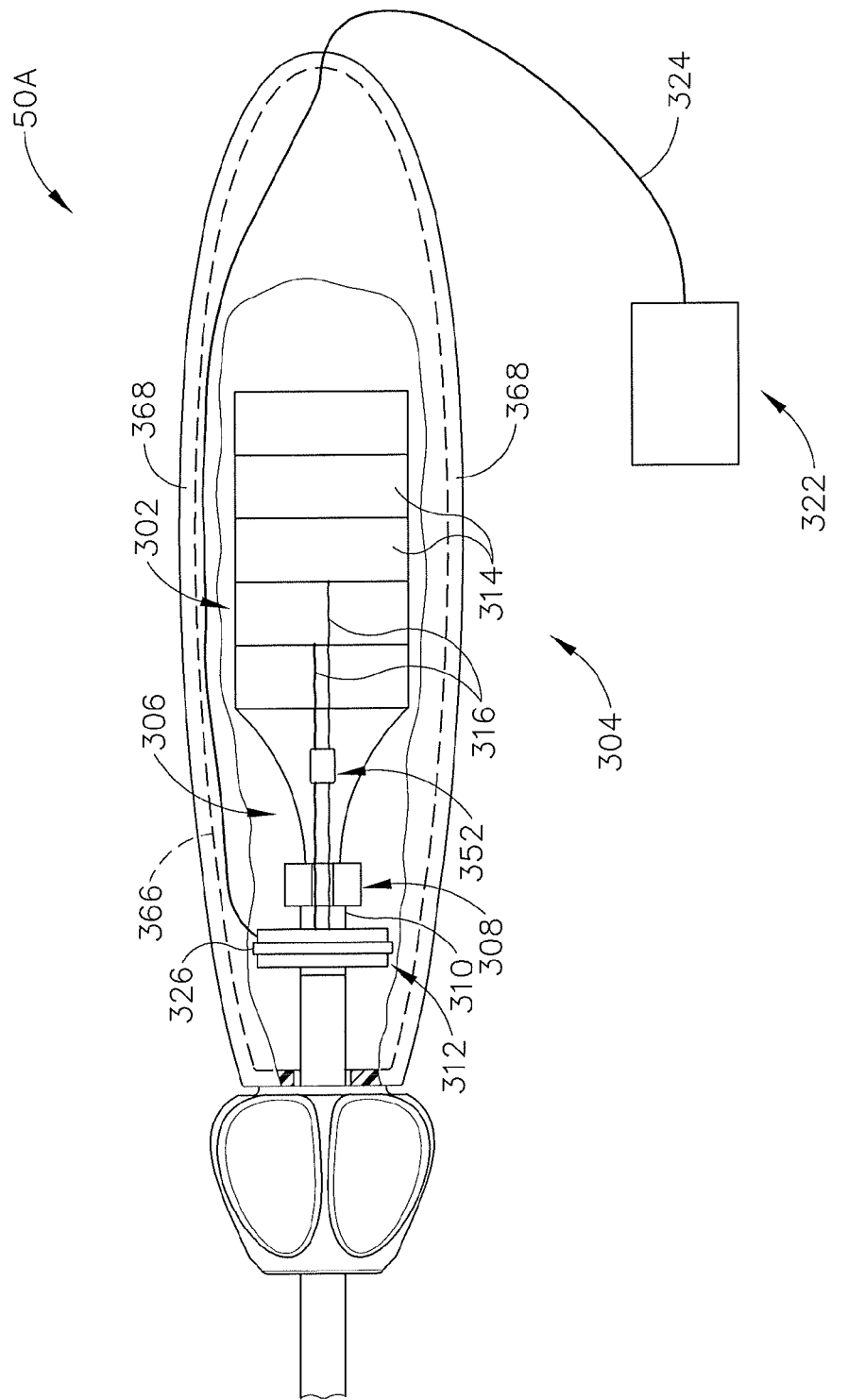
FIG. 8 depicts a plan view of an exemplary surgical instrument having clam-shell shaped interior surfaces to house electrical conduits.

FIG. 8 shows a top plan view of a version of surgical instrument (50A) additionally including a connector such as two-prong connector (352) described above. Handpiece assembly (304) is divisible into a pair of shroud halves (368), which present interior surfaces (366). Interior surfaces (366) are cylindraceous surfaces having a clamshell shape. The clamshell shaped regions of interior surfaces (366) provide smooth and outwardly bowed interior surfaces to face transducer (302). Interior surfaces (366) may surround all features that could otherwise potentially lead to snagging or other types of mechanical interference during a rotational movement of drum (312) and transducer (302), such as conduit (324). For example, the smoothness of interior surfaces (366) reduces the likelihood that wires such as conduit (324) will be snagged as transducer (302) is rotated within handpiece assembly (304). Of course, the interior surfaces of handpiece assembly (304) may have any other suitable shapes, structures, features, configurations, etc.

C. Exemplary Pocket in Mounting Ring

FIGS. 9-10 show a version of a mounting ring (382) that includes a proximal mount (381) having a pocket (380). Mounting ring (382) is mounted on horn (310) of transducer (302) in this example, though it should be understood that mounting ring (382) may instead be mounted on some other portion of transducer (302). It should also be understood that mounting ring (382) may be used as a variation of mounting ring (308) in instrument (50A). Pocket (380) is configured to receive and retain a fitted two-prong connector (352). Two-prong connector (352) may be press-fit into pocket (380) in proximal mount (381) or may be otherwise coupled with proximal mount (381).

Two-prong connector (352) is operable to couple wires (316A) extending from drum (312) with a mating connector (374). In particular, two-prong connector (352) includes prongs (376) configured to mate in the direction of arrow (A), or a reversed direction, with sockets (378) of mating connector (374) to provide an electrical coupling between two-prong connector (352) and mating connector (374). Mating connector (374) is coupled with wires (316B) extending from piezoelectric elements (314) of transducer (302).

It should be understood that, as with any other wires referred to herein, wires (316A, 316B) may be replaced with a flex-circuit and/or other type of conductive structure/feature. In the present example, wires (316A) travel within one or more channels (not shown) disposed along mounting ring (372) to enable one or more bearings to encompass mounting ring (372) without encountering interference from wires (316A). In some versions, wires (316A) travel along an exterior of mounting ring (382) from drum (312) to connector (352).

Mounting ring (382) of the present example also includes distal mount (383) that is coupled between proximal mount (381) and drum (312). Of course, distal mount (383) and proximal mount (381) may be consolidated into a monolithic structure if desired. In the present example, proximal mount (381) extends along a length nearly reaching piezoelectric elements (314) of transducer (302), to reduce the likelihood of wires (316B) contacting horn (310) or piezoelectric elements (314). Other suitable configurations will be apparent to those of ordinary skill in the art in view of the teachings herein.

D. Exemplary Press-Fit Cap

Figure 11:
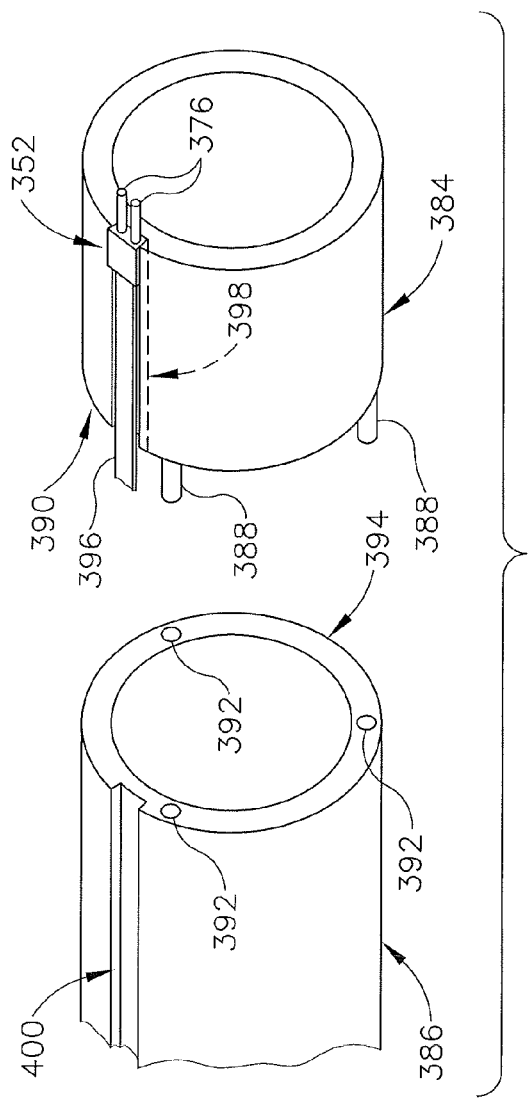
FIG. 11 depicts a perspective view of an exemplary mounting ring and an exemplary proximal cap.
Figure 12:
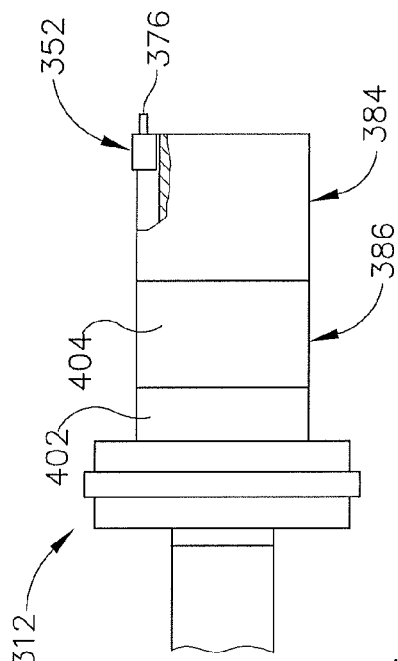
FIG. 12 depicts an elevation view of the assembled exemplary mounting ring and proximal cap of FIG. 11.

FIGS. 11 and 12 show proximal cap (384) attachable to mounting ring (386). Mounting ring (386) may be used as a variation of mounting ring (308) in instrument (50A). In particular, pins (388) extending from distal end (390) of proximal cap (384) are configured and sized for receipt in apertures (392) in proximal end (394) of mounting ring (386) to retain proximal cap (384) to mounting ring (386) in a press-fit type of configuration. Proximal cap (384) may comprise plastic or any other suitable material.

Proximal cap (384) includes a two-prong connector (352) connected to flex circuit (396). Flex circuit (396) is disposed in channel (398) of proximal cap (384) and channel (400) of mounting ring (386) when proximal cap (384) is attached to mounting ring (386). Flex circuit (396) ultimately leads to a drum such as drum (312) described above, such that flex circuit (396) ultimately couples connector (352) with a power source (e.g., generator (322), as described above) via a slip ring assembly (e.g., contact assembly (318), as described above). Mounting ring (396) comprises distal mount (402) attached to proximal mount (404) as two separate components, though it should be understood that mounting ring (386) may alternatively comprise a unitary, monolithic material formed as a single component.

Proximal cap (384) acts as a custom pin connector holder or arm that may be snap-fitted into proximal end (394) of mounting ring (386). Proximal cap (384) may thus serve as a carrier for flex circuit (396) connections between drum (312) and transducer (302) that may either be routed on an outside circumference of proximal cap (384) or within a surface defined in proximal cap (384).

E. Exemplary Flex Circuit Harness

Figure 13:
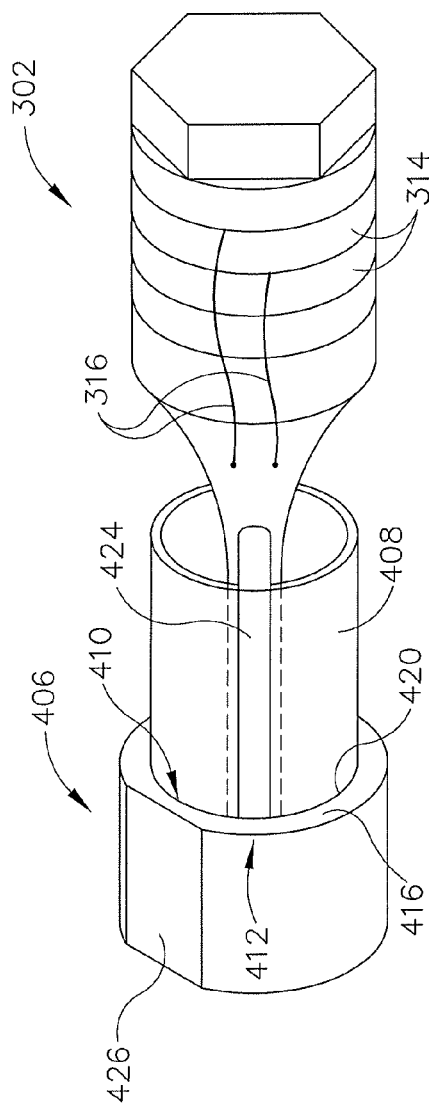
FIG. 13 depicts a perspective view of an exemplary mounting ring and harness assembly of an exemplary rotatable assembly.
Figure 14:
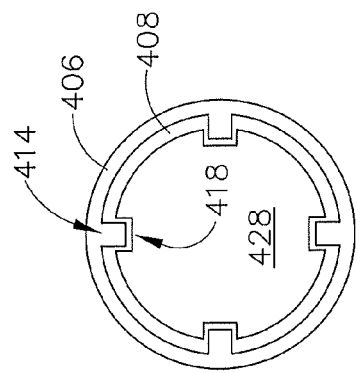
FIG. 14 depicts an end view of the mounting ring and harness assembly of FIG. 13.

FIGS. 13-14 show a version of mounting ring (406) including a flex circuit harness (408). Mounting ring (406) may be used as a variation of mounting ring (308) in instrument (50A). Harness (408) of the present example comprises a tube formed of plastic or any other suitable material. Distal end (410) of harness (408) attaches to proximal end (412) of mounting ring (406). For example, as shown in FIG. 14, tabs (414) from proximal surface (416) of proximal end (412) of mounting ring (406) are configured for a retaining receipt in slots (418) disposed within distal surface (420) of distal end (410) of harness (408) to retain mounting ring (406) against harness (408) in a press-fit connection.

Harness (408) is disposed between transducer (302) and flex circuit (424), which extends from mounting ring (406) and is configured for attachment to wires (316). Harness (408) supports flex circuit (424) and prevents flex circuit (424) from contacting horn (310) and/or other parts of transducer (302). Flex circuit (424) may be routed through or over mounting ring (406). For example, mounting ring (406) includes flattened surface (426) which facilitates ease of routing flex circuit (424) over mounting ring (406).

Harness (408) acts as a mechanical shield to rotating transducer (302) from the electrical conduits such as flex circuit (424) that is routed over mounting ring (406) to piezoelectric elements (314). Harness (408) may additionally act as a holder for a connector such as two-prong connector (352), which may be attached to a portion of harness (408) configured to receive connector (352) in a press-fit connection, for example. Connector (352) may then be mated to an electrical connector (not shown) of transducer (302), and the electrical connector may be connected to wires (316). The electrical conduits may be routed on an outside of harness (408) or within an interior surface defining aperture (428) of harness (408).

F. Exemplary Shaped Channels in Mounting Ring

Figure 15:
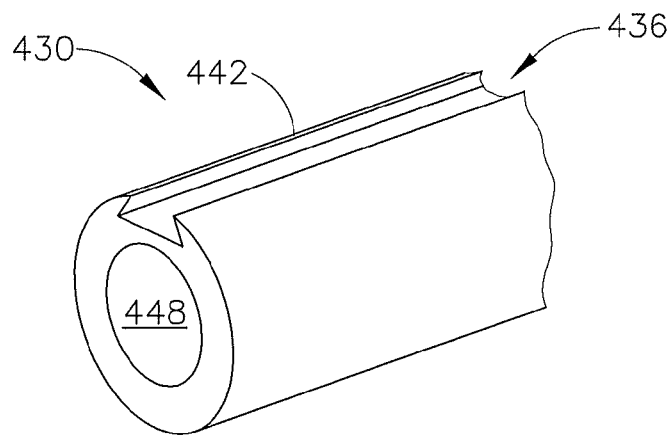
FIG. 15 depicts a perspective view of an exemplary mounting ring having a channel with a dovetail cross-sectional shape.
Figure 16:
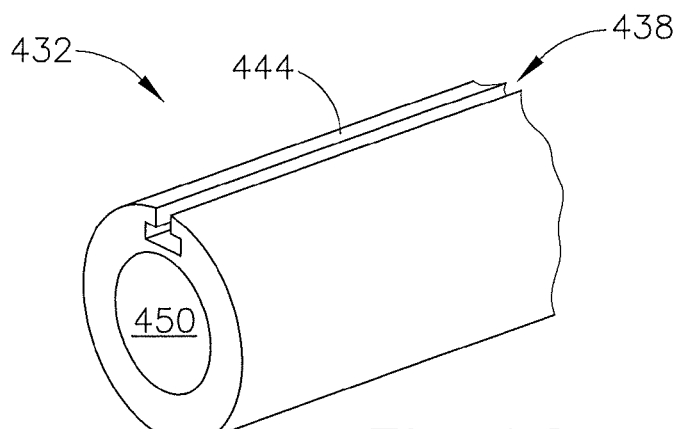
FIG. 16 depicts a perspective view of an exemplary mounting ring having a channel with a T-shaped cross-sectional shape.
Figure 17:
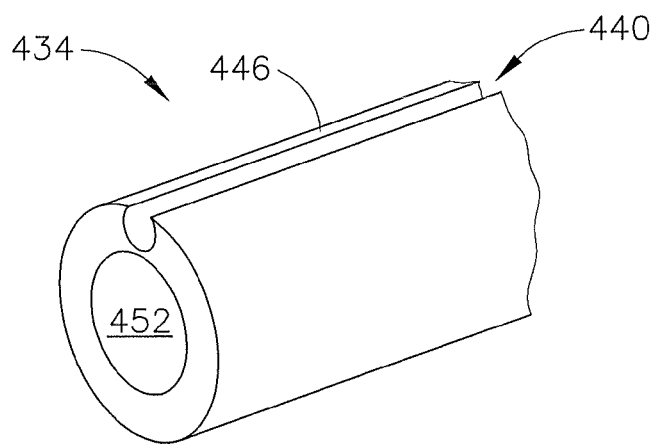
FIG. 17 depicts a perspective view of an exemplary mounting ring having a channel with a circular cross-sectional shape.

FIGS. 15-17 respectively show mounting rings (430, 432, 434). Mounting rings (430, 432, 434) may be used as respective variations of mounting ring (308) in instrument (50A). Mounting rings (430, 432, 434) respectively include channels (436, 438, 440) defined in respective surfaces (442, 444, 446). Mounting rings (430, 432, 434) respectively include apertures (448, 450, 452) configured for receipt of horn (310) of transducer (302), for example.

Channels (436, 438, 440) are configured to receive electrical conduits (not shown), such as, for examples, wires (316) from FIG. 5. The electrical conduits over respective mounting rings (430, 432, 434) may be retained and fixed in channels (436, 438, 440) in such a way as to not interfere with the rotational movement of transducer (302). The channels may be machined into respective mounting rings in a variety of shapes and be configured to retain electrical conduits such as wires (316). For example, channel (436) of mounting ring (430) includes a dovetail shape, channel (438) of mounting ring (432) includes a T-shape cut, and channel (440) of mounting ring (434) includes a circular aperture shape. Rectangular cross-sectional shapes and any other suitable shapes apparent to those of ordinary skill in the art in view of the teachings herein are possible.

G. Exemplary Channels in Mounting Ring and/or Retained Components

FIGS. 18-29 depict different versions of exemplary channels and/or retained components that are features of one or more mounting rings. The below-described mounting rings are variations of mounting ring (508) described above for instrument (50A). Similarly, the mounting rings structurally support transducer (302) while permitting transducer (302) to rotate relative to handpiece assembly (304). In the examples below, FIGS. 18-29 show flex circuits for connection with transducer (302). The flex circuits are disposable in the respective channels of the mounting rings of FIGS. 18-29. Retention of the flex circuits in such channels reduces the likelihood of the flex circuits interfering with rotation of transducer (302) and the respective associated mounting ring. Additionally or alternatively to flex circuits, the mounting rings of FIGS. 18-29 may be used to retain wires and/or like components, such as those shown within the mounting rings of described above for FIGS. 7-17.

1. Exemplary Track Snap Component

Figure 18:
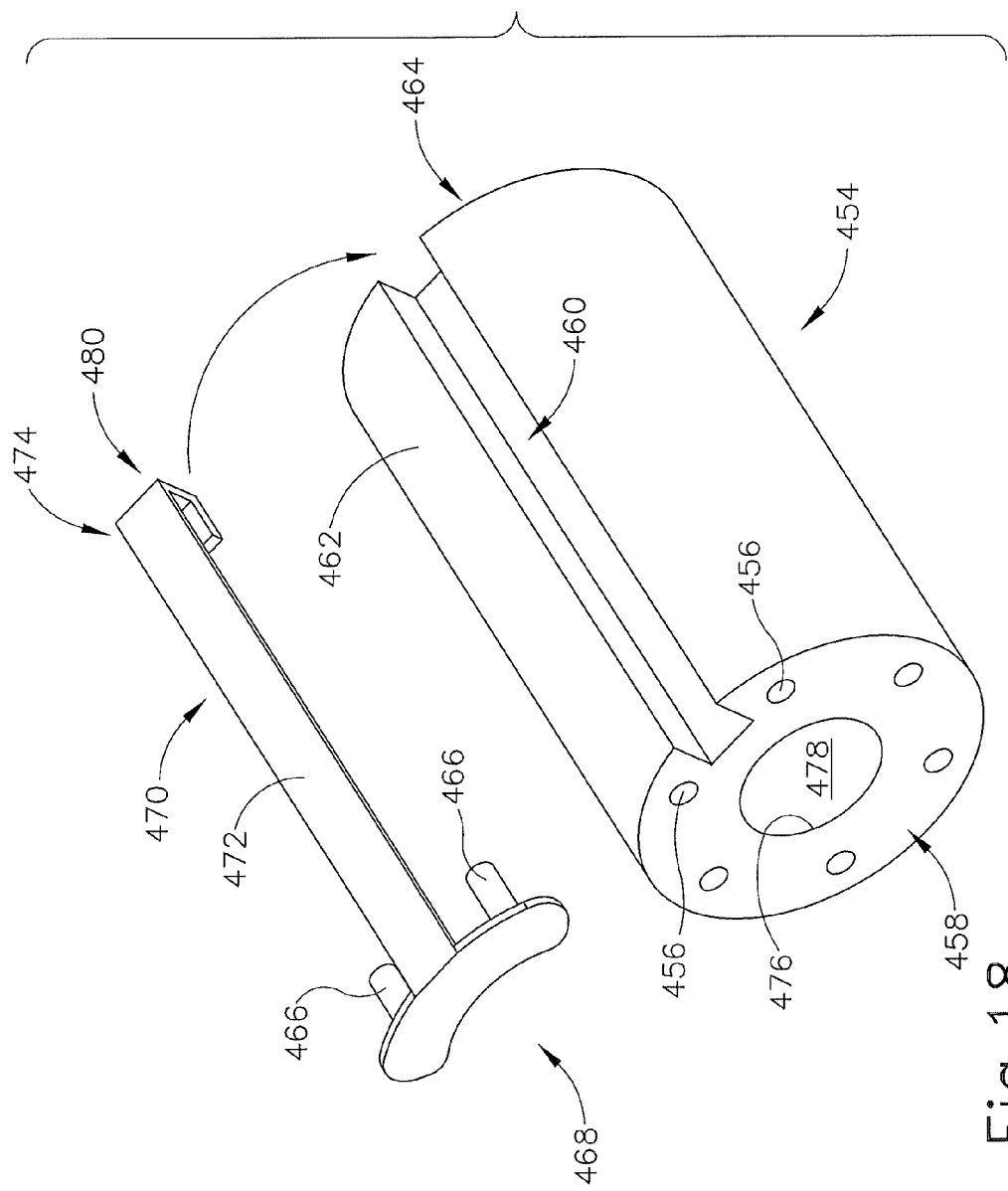
FIG. 18 depicts a perspective view of an exemplary mounting ring and snap-fit flex circuit assembly.

FIG. 18 shows mounting ring (454) including apertures (456) at distal end (458) and channel (460) disposed on exterior surface (462) of mounting ring (454) between distal end (458) and proximal end (464). Mounting ring (454) may be used as a variation of mounting ring (308) in instrument (50A). Apertures (456) are configured for receipt of prongs (466) of distal end (468) of flex circuit retainer (470), which is a component that retains and covers a separate flex circuit (not shown) in channel (460). Flex circuit retainer (470) may be formed of plastic and/or any other suitable material(s). Elongate bar (472) of flex circuit retainer (470) extends between distal end (468) and proximal end (474) of flex circuit retainer (470). Channel (460) of mounting ring (454) is sized and configured to receive elongate bar (472) of flex circuit retainer (470). Mounting ring (454) also includes interior wall surface (476) defining aperture (478). At proximal end (474), flex circuit retainer (470) includes L-shaped protrusion (480) configured to latch to interior wall surface (476) of mounting ring (454) to additionally retain flex circuit retainer (470) to mounting ring (454). In particular, L-shaped protrusion (480) received against interior wall surface (476) at proximal end (464) of mounting ring (454) provides an opposing force against the receipt of prongs (466) of flex circuit retainer (470) within apertures (456) at distal end (458) of mounting ring (454) to provide a snap-fit connection. Flex circuit retainer (470) or mounting ring (454) may be modified to include retention features for a connector, such as connector (352), as well. The surface of elongate bar (472) of flex circuit retainer (470) may be substantially flush with exterior surface (462) of mounting ring (454) such that placement of flex circuit retainer (470) completes the outer circumference of mounting ring (454) in a relatively seamless fashion. Thus, the assembly of flex circuit retainer (470) and mounting ring (454) may freely rotate within a bearing without interference from flex circuit retainer (470) and/or other wires.

2. Exemplary FEP Sleeve or Snap-Fit Components

FIGS. 19-21 show versions of a mounting ring with additional exemplary components that may be used to secure and/or retain wires, flex circuits, etc., against the exterior of a mounting ring and/or within a channel in a mounting ring. In particular, FIG. 19 shows mounting ring (482) including aperture (484) configured to receive a transducer horn such as horn (310) described above. Mounting ring (482) may be used as a variation of mounting ring (308) in instrument (50A). Mounting ring (482) includes channel (486) defined in exterior surface (488) of mounting ring (482). Single snap-fit component (490) is configured to surround exterior surface (488) of mounting ring (482). Single snap-fit component (490) includes a pair of prongs (492) configured to be received into channel (486) to connect single snap-fit component (490) to channel (486) to assist with retention of any electrical conduits, such as wires (316), within channel (486). Component (490) may be formed of a resilient plastic and/or any other suitable material(s).

FIG. 20 shows mounting ring (494) including aperture (496) configured to receive horn (310). Mounting ring (494) may be used as a variation of mounting ring (308) in instrument (50A). Mounting ring (494) includes opposing channels (498, 500) defined in exterior surface (502) of mounting ring (494). Dual snap-fit component (504) includes first portion (506) and second portion (508), and each portion is respectively configured to surround opposing sides of exterior surface (502) between channels (498, 500) of mounting ring (482). First portion (506) includes prongs (510, 512) configured to be respectively received into channels (498, 500) to connect first portion (506) to mounting ring (482) to assist with retention of any electrical conduits, such as wires (316), within channels (498, 500). Similarly, second portion (508) includes prongs (514, 516) configured to be respectively received into channels (498, 500) to connect second portion (508) to mounting ring (482) to assist with retention of any electrical conduits, such as wires (316), within channels (498, 500). Component (504) may be formed of a resilient plastic and/or any other suitable material(s).

FIG. 21 shows mounting ring (518) including aperture (520) configured to receive horn (310). Mounting ring (518) may be used as a variation of mounting ring (308) in instrument (50A). Mounting ring (518) includes channel (522) defined in exterior surface (524) of mounting ring (518). Sleeve component (526) comprises plastic or any other suitable material. The plastic material may be comprised of a fluoropolymer such as fluorinated ethylene propylene (FEP), or any other suitable fluoropolymer. FEP is a copolymer of hexafluoropropylene and tetrafluoroethylene that includes the properties of low friction and non-reactivity. FEP sleeve component (526) is configured to surround exterior surface (524) and have protrusion (528) configured for a press-fit receipt in channel (522) of mounting ring (518). Such a connection assists with retention of any electrical conduits, such as wires (316), within channel (522).

The outer surfaces of single snap-fit component (490), dual snap-fit component (504), or FEP sleeve component (526) complete an outer circumference of respective mounting rings (482, 494, 518) to allow the assembly formed by components (490, 504, 526) and mounting rings (482, 494, 518) to rotate freely within a bearing supporting the respective mounting rings.

3. Exemplary Dual-Channel Cap

Figure 22:
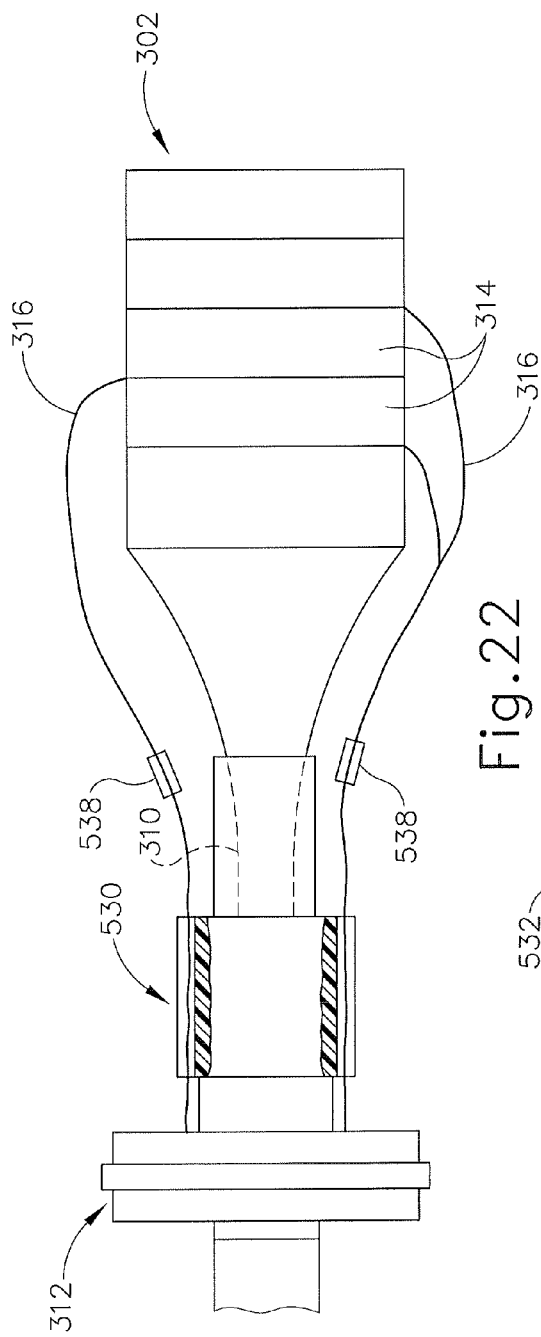
FIG. 22 depicts an elevation view of an exemplary rotatable assembly and a cap.
Figure 23:
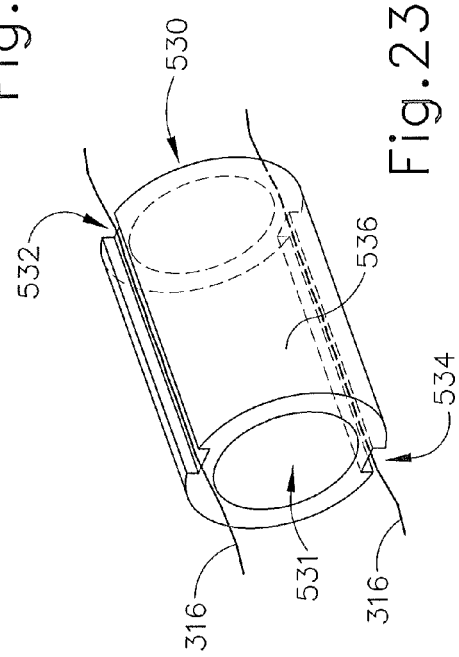
FIG. 23 depicts a perspective view of the cap of FIG. 22.

FIGS. 22-23 show an exemplary cap (530) comprising plastic, though other suitable materials are possible. Plastic cap (530) including aperture (531) surrounds an exterior of a mounting ring, or may act as a mounting ring, on horn (310). The mounting ring may be mounting ring (308) or a variation described herein. Plastic cap (530) includes opposing dual channels (532, 534) defined in exterior surface (536) of cap (530). Wires (316) include spade lugs (538), which provide quick electrical connections by selectively plugging into corresponding sockets of cap (530). Of course, any other suitable type of electrical coupling may be used. Wires (316) extend between drum (312) and transducer (302) through channels (532, 534) of cap (530), proximal to the sockets.

4. Exemplary Retention Clips

FIG. 24 shows mounting ring (540) disposed on horn (310) of transducer (302). Mounting ring (540) may be used as a variation of mounting ring (308) in instrument (50A). Mounting ring (540) includes first portion (542) including annular channels (544, 546) and second portion (548) including annular channel (550). Alternatively, mounting ring (540) may include only first portion (542).

Annular channels (544, 546, 550) are each configured to receive a retention device. For example, the retention device may be one or more o-rings disposed over flex circuit (554), or retention clip (556) as shown in FIGS. 25-26. Retention clip (556) may be disposed over a flex circuit or wire, such as flex circuit (554), which is disposed in longitudinal channel (547) of mounting ring (540). Retention clip (556) may include semi-annular U-shaped portion (558) having intermediate, central surface (560) from which bar (562) transversely extends. U-shaped portion (558) may be configured to be received in one of channels (544, 546, 550) while bar (562) is configured for receipt within an axially oriented channel of mounting ring (540), which is substantially aligned with a longitudinal axis of mounting ring (540).

Channels (544, 546, 550) may be additional to other axially oriented channels formed in mounting ring (540) to retain electrical conduits. The additional channels would allow for the addition of retention devices such as o-rings comprised of rubber or any other suitable material or retention clips (556) comprised of plastic or any other suitable material.

5. Exemplary Drum and Cap Assembly

FIG. 27-29 show a version of mounting ring (564) with plastic cap (566) configured to snap over channel (568) defined in mounting ring (564). Mounting ring (564) may be used as a variation of mounting ring (308) in instrument (50A). Mounting ring (564) and cap (566) are configured to be disposed over horn (310) and are positioned proximal to drum (312) and distal to transducer (302). Cap (566) may include tabs configured to fit into slots of mounting ring (564) to connect cap (566) to mounting ring (564). Alternatively, slots in cap (566) may be configured to receive tabs of mounting ring (564).

FIG. 28 shows a cross-sectional view of mounting ring (564) taken along line 28-28 with a pair of channels (568A, 568B) defined in mounting ring (564). FIG. 29 shows mounting ring (564) including channels (568A, 568B) with flex circuit (570) received in channel (568A). Cap (566) is configured to be positioned over flex circuit (570) to retain flex circuit (570) within channel (568A) when transducer (502) rotates, for example. Alternatively, flex circuit (570) may including a connector such that flex circuit (570) and connector are preassembled onto a channel defined in cap (566) to retain wires such as wires (316) and connector(s) from shroud halves (368) and horn (310).

H. Exemplary Alternative Channel Assemblies in Mounting Ring

FIGS. 30-36 show versions of mounting rings that may include various channels and/or components that may be used to secure and/or retain wires, flex circuits, etc., against the exterior of a mounting ring or within a channel if included. Various ways in which the below teachings may be combined with teachings from above and teachings from various references cited herein will be apparent to those of ordinary skill in the art.

1. Exemplary Shrink Tube Assembly

Figure 30:
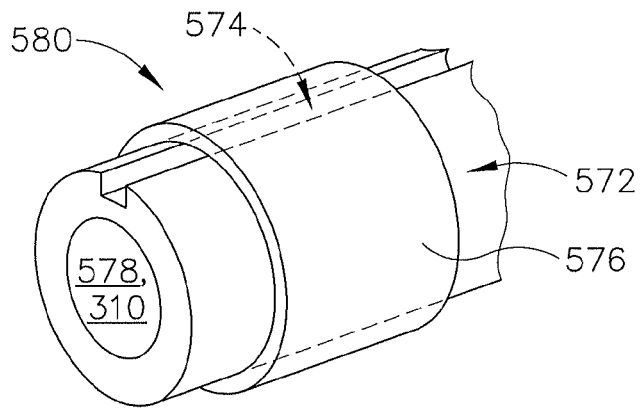
FIG. 30 depicts a fragmentary, perspective view of an exemplary mounting ring and tube assembly.

FIG. 30 shows mounting ring (572) having channel (574) defined in exterior surface (576) and aperture (578) configured to retain horn (310) of transducer (302). Mounting ring (572) may be used as a variation of mounting ring (308) in instrument (50A). A large diameter heated shrink tube or outer band (580) is annularly disposed about exterior surface (576) of a proximal portion of mounting ring (572) such that a portion of shrink tube (580) covers channel (574) to retain electrical conduits such as wires (316), a flex circuit, and/or a connector within channel (574). Additionally or alternatively, one or more electrical conduits may be disposed against exterior surface (576) of mounting ring (572). Further, an alternate version of mounting ring (572) may lack a channel (574). Outer band (580) of the present example is resiliently biased to compress and shrink against mounting ring (572), such that outer band (580) resiliently covers channel (574). It should be understood that outer band (580) may be readily used in combination with the examples shown in FIGS. 15-17, described above, among other configurations.

2. Exemplary Adhesive Assembly

Figure 31:
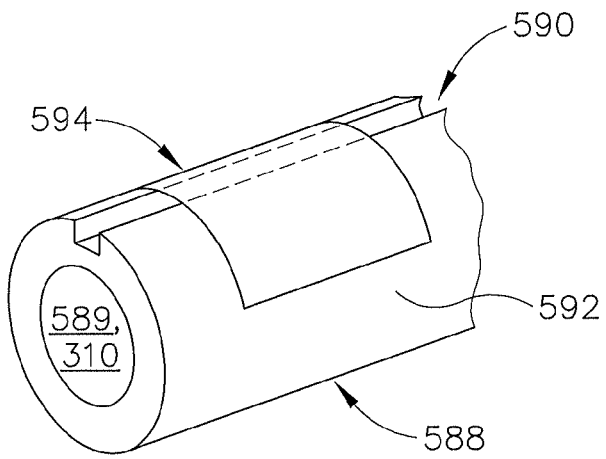
FIG. 31 depicts a perspective view of an exemplary mounting ring including a channel and an adhesive disposed over the channel.

FIG. 31 shows mounting ring (588) including aperture (589) configured to receive horn (310) of transducer (302). Mounting ring (588) may be used as a variation of mounting ring (308) in instrument (50A). Mounting ring (588) includes channel (590) disposed in exterior surface (592) such that channel (590) is configured to receive one or more electrical conduits such as wires, a flex circuit, and/or a connector. Adhesive (594), which may comprise a sticker, glue, and/or any other suitable adhesive material, covers a portion of channel (590) to retain electrical conduits within channel (590). Adhesive (594) may be comprised of adhesive such as, but not limited to, polymerizable and/or cross-linkable materials such as a cyanoacrylate adhesive or any other suitable type of adhesive known to those of skill in the art in view of the teachings herein. It should be understood that adhesive (594) may be readily used in combination with the examples shown in FIGS. 15-17, described above, among other configurations.

3. Exemplary Tabs in Channel Assembly

Figure 32:
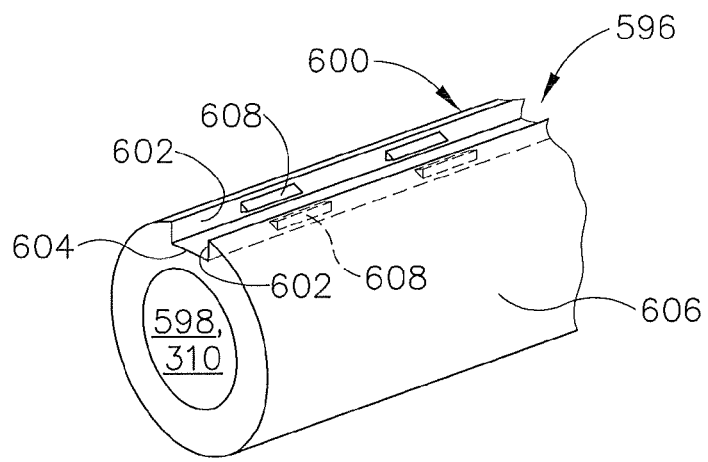
FIG. 32 depicts a perspective view of an exemplary mounting ring including a channel having opposing tabs for retention of electrical conduits.

FIG. 32 shows mounting ring (596) including aperture (598) configured to receive horn (310) of transducer (302). Mounting ring (596) may be used as a variation of mounting ring (308) in instrument (50A). Mounting ring (596) includes channel (600) defined by mutually-facing sidewalls (602) and intermediate wall (604) disposed between sidewalls (602) where sidewalls (602) and intermediate wall (604) are disposed within exterior surface (606) of mounting ring (596). Pairs of opposing tabs (608) project from sidewalls (602) to assist with retaining one or more electrical conduits such as wires, a flex circuit, and/or a connector within channel (600). Such electrical conduits may be snapped, clicked, or otherwise deformed into channel (600) past tabs (608) to rest and be retained between intermediate wall (604) and tabs (608). An adhesive and/or an outer band, as described above, may be positioned over channel (600) to further retain the electrical conduit in channel (600) to assure the electrical conduit will maintain its desired positioning.

Additionally, a channel's cross-section may be shaped to assist with retention of the electrical conduit. For example, the channel may be shaped as a dovetail, a T-shape, or other suitable shape, as described in greater detail below, and the electrical conduits may then be glued into the shaped channel. It should be understood that tabs (608) may be readily used in combination with the examples shown in FIGS. 15-17, described above, among other configurations.

4. Exemplary Keyhole Flex Mounting Assembly

Figure 34:
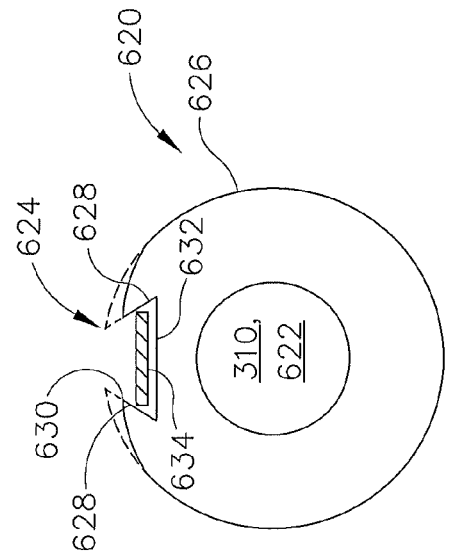
FIG. 34 depicts an end view of an exemplary mounting ring having an alternative keyed channel including a dovetail cross-sectional shape, and a flex circuit disposed within and retained by edges of the channel.
Figure 33:
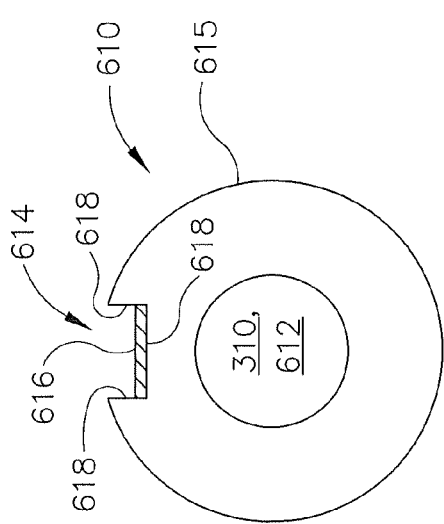
FIG. 33 depicts an end view of an exemplary mounting ring having a keyed channel including a rectangular cross-sectional shape, and a flex circuit disposed and retained within the channel.

FIGS. 33-34 show mountings rings with different types of shapes machined into exterior surfaces to form channels configured to receive electrical conduits. It should be understood that the channel configurations shown in FIGS. 33-34 may be used in combination with or in lieu of the channel configurations shown in FIGS. 15-17. It should also be understood that the various retention features described above with reference to FIGS. 30-32 may be readily combined with the channels shown in FIGS. 33-34. Various other suitable ways in which the teachings herein may be combined will be apparent to those of ordinary skill in the art.

FIG. 33 shows mounting ring (610) including aperture (612) configured to receive horn (310) of transducer (302). Mounting ring (610) may be used as a variation of mounting ring (308) in instrument (50A). Channel (614) is defined in exterior surface (615) of mounting ring (610). Channel (614) is configured to key to and receive an electrical conduit such as flat flex circuit (616) such that flex circuit (616) is securely retained within walls (618) defining channel (614) in a press-fit manner. Alternatively, channel (614) may be formed as a T-slot (not shown) having a T-shaped cross-sectional configuration with a relatively larger cross-sectional width a lower portion of the T-slot, and a relatively smaller cross-sectional width in an upper portion of the T-slot. Flex circuit (616) may be sized to freely fit into the larger lower portion after being bent/deformed and pushed past the smaller upper portion of the T-slot. Flex circuit (616) may thus be wider than the smaller upper portion of the T-slot and may be formed of a resilient material.

FIG. 34 shows mounting ring (620) including aperture (622) configured to receive horn (310) of transducer (302). Mounting ring (620) may be used as a variation of mounting ring (308) in instrument (50A). Channel (624) is defined in exterior surface (626) of mounting ring (620). Interiorly angled walls (628) having edges (630) and intermediate wall (632) define channel (624). The portion of exterior surface (626) in which channel (624) is defined may include flattened surfaces (shown in solid lines versus the more rounded phantom lines) to reduce an opportunity for edges (630) to be caught in portions of the housing of handpiece assembly (304) when transducer (302), drum (312), and mounting ring (620) disposed on transducer (302) are rotating, or rather to reduce the opportunity of the electrical conduit to interfere with the rotational movement of transducer (302) and mounting ring (620) within the shroud halves of handpiece assembly (304). Edges (630) may additionally or alternatively be rounded to similarly reduce such opportunities. Channel (624) is configured to receive and retain electrical conduit, as edges (630) are disposed over portions of the electrical conduit, such as flex circuit (634), such that flex circuit (634) is securely retained within walls (628, 632) defining channel (624).

5. Exemplary Pins in Channel Assembly

Figure 35:
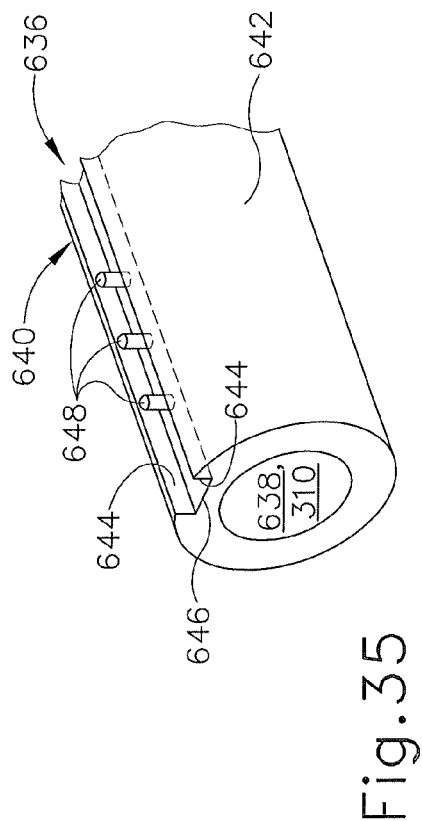
FIG. 35 depicts a perspective view of an exemplary mounting ring including a channel having protruding pins for retention of electrical conduits.
Figure 36:
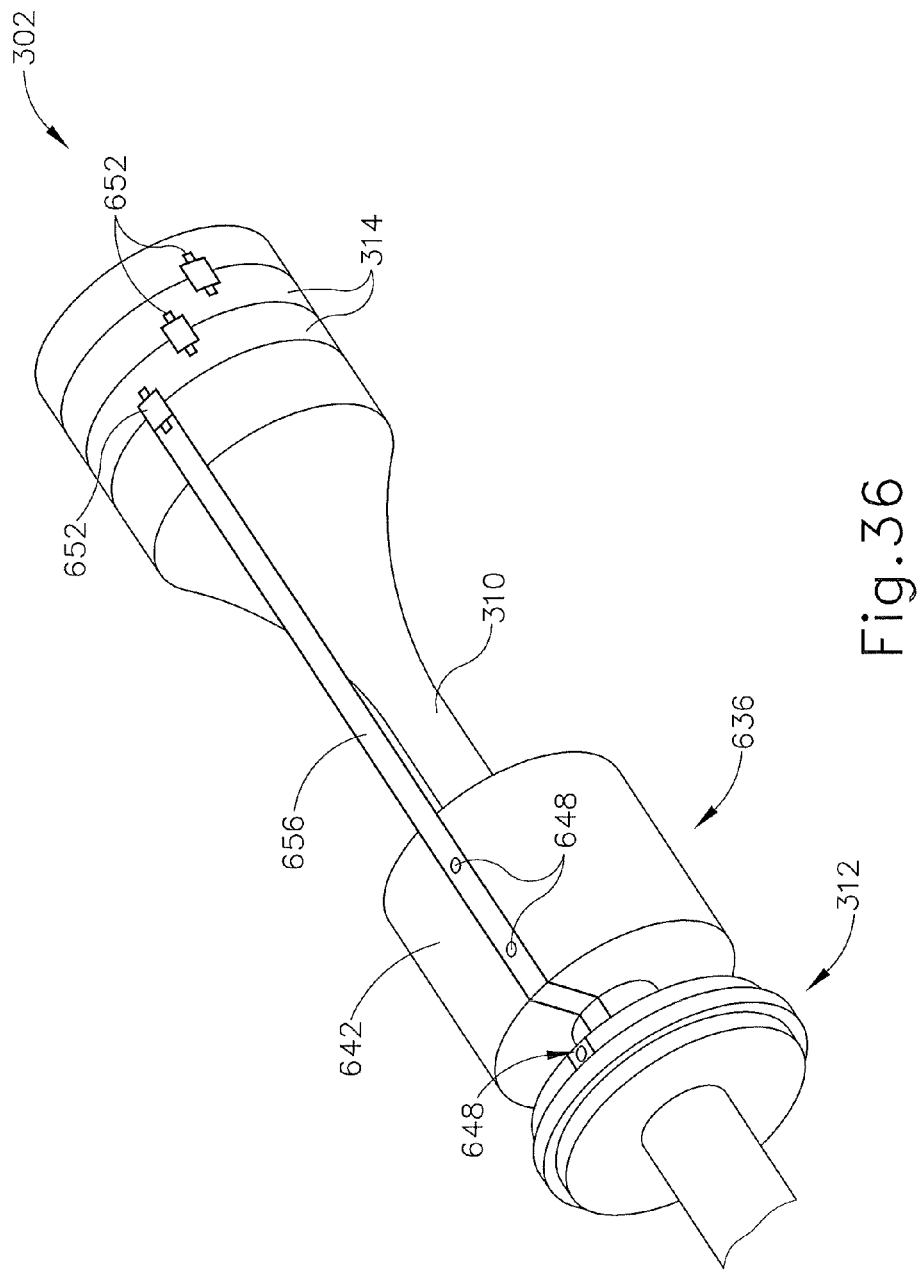
FIG. 36 depicts a perspective view of an exemplary rotatable assembly including the mounting ring of FIG. 35 engaged with a flex circuit.

FIGS. 35-36 show another exemplary mounting ring (636). As shown in FIG. 35, mounting ring (636) of this example includes an aperture (638) configured to receive horn (310) of transducer (302). A channel (640) is defined in exterior surface (642) of mounting ring (636). Interiorly opposed sidewalls (644) include intermediate wall (646) disposed therebetween such that sidewalls (644) and intermediate wall (646) together define channel (640). FIG. 36 shows mounting ring (636) disposed about horn (310) of transducer (302), which has electrical contacts (652) positioned on piezoelectric elements (314) of transducer (302). Mounting ring (636) may be used as a variation of mounting ring (308) in instrument (50A).

Channel (640) of mounting ring (650) in the present example is configured to receive an electrical conduit such as flex circuit (656). Each electrical contact (652) receives a respective flex circuit (656). It should therefore be understood that mounting ring (650) may include separate channels (640) for each flex circuit (656). Pins or plugs (648) protrude from the channel (640) of mounting ring (636) to interferingly fit within corresponding holes formed through flex circuit (656). Such plugs (648) may thus assist in retaining flex circuit (656) within channel (640). Additionally or alternatively, flex circuit (656) itself may have pins assisting to securely position flex circuit (656) when the pins are received in corresponding holes in mounting ring (650).

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical instrument comprising:
 (a) a body;
 (b) a transmission assembly extending distally from the body;
 (c) an end effector coupled to a distal end of the transmission assembly;
 (d) an ultrasonic transducer in acoustic communication with the end effector via the transmission assembly such that the transducer, the transmission assembly, and the end effector together define an acoustic assembly;
 (e) a mounting ring rotatably coupling the transducer with the body, wherein one or more piezoelectric components of the transducer are disposed proximally of the mounting ring;
 (f) a drum disposed distally of the mounting ring; and
 (g) one or more electrical conduits coupling the drum with the piezoelectric components, wherein the electrical conduits are routed over or through the mounting ring.

2. The surgical instrument of claim 1, wherein the drum is rotatable, wherein the body comprises an electrical contact assembly configured to receive power from a generator, wherein the electrical contact assembly is resiliently biased against the rotatable drum.

3. The surgical instrument of claim 2, wherein the drum, the mounting ring, and the transducer together comprise a unitarily rotatable assembly.

4. The surgical instrument of claim 3, wherein the body further comprises shroud halves, wherein the shroud halves comprise smooth interior surfaces facing the transducer configured to retain a set of electrical conduits to prevent interference of the set of electrical conduits with the rotatable assembly when the rotatable assembly rotates within the shroud halves.

5. The surgical instrument of claim 1, wherein the one or more electrical conduits comprise at least one of wires or flex circuits.

6. The surgical instrument of claim 1, wherein the mounting ring comprises one or more prongs and one or more tabs projecting from the one or more prongs, wherein the one or more tabs are configured for receipt within one or more notches within an interior surface of a clip to retain the mounting ring to the clip in a snap-fit connection.

7. The surgical instrument of claim 6, wherein the body comprises a handle assembly.

8. The surgical instrument of claim 1, wherein the mounting ring comprises one or more channels disposed in the mounting ring, wherein the one or more channels are configured to receive the one or more electrical conduits.

9. The surgical instrument of claim 8, wherein at least one channel is configured to receive at least one electrical conduit in a snap-fit connection.

10. The surgical instrument of claim 8, wherein the one or more channels has a cross-section that is one of T-shaped, dovetail-shaped, circular, or rectangular.

11. The surgical instrument of claim 8, wherein the one or more channels comprise at least one of pins or tabs configured to retain the one or more electrical conduits within the one or more channels.

12. The surgical instrument of claim 8, further comprising an adhesive disposed over the one or more channels to retain the one or more electrical conduits within the one or more channels.

13. The surgical instrument of claim 8, further comprising a cap attached to a proximal end of the mounting ring, the cap comprising one or more channels coaxially aligned with the one or more channels of the mounting ring, wherein the cap comprises a pocket at a proximal end of the cap, the pocket being configured to receive a two-prong connector.

14. The surgical instrument of claim 8, further comprising an outer band disposed over the mounting ring to retain the one or more electrical conduits within the one or more channels.

15. The surgical instrument of claim 8, further comprising one or more annular channels configured to receive a retention member configured to retain the one or more electrical conduits.

16. A surgical instrument comprising:
(a) a handle assembly;
(b) an acoustic transmission assembly comprising:
  i. a shaft extending distally from the handle assembly, and
  ii. an end effector coupled to a distal end of the shaft, wherein the end effector includes a harmonic blade; and
(c) a transducer in acoustic communication with the end effector;
(d) a mounting ring rotatably coupling the transducer with the handle assembly, the mounting ring having one or more channels disposed in the mounting ring, wherein the transducer has one or more piezoelectric components disposed proximally of the mounting ring;
(e) a drum disposed distally of the mounting ring; and
(f) one or more electrical conduits coupling the drum with the piezoelectric components, wherein the electrical conduits are disposed within and routed through the one or more channels in mounting ring.

17. The surgical instrument of claim 16, further comprising at least one retention member retaining the electrical conduits within the one or more channels.

18. The surgical instrument of claim 16, wherein the transducer includes a horn, wherein the mounting ring is mounted to the horn.

19. The surgical instrument of claim 16, further comprising a power source, wherein the handle assembly includes a slip ring assembly coupling the drum with the power source.

20. A surgical instrument comprising:
(a) a handle assembly;
(b) an acoustic transmission assembly comprising:
  i. a shaft extending distally from the handle assembly, and
  ii. an end effector coupled to a distal end of the shaft, wherein the end effector includes a harmonic blade; and
(c) a transducer in acoustic communication with the end effector;
(d) a mounting ring rotatably coupling the transducer with the handle assembly, the mounting ring having one or more channels disposed in the mounting ring, wherein the transducer has one or more piezoelectric components disposed proximally of the mounting ring;
(e) a drum disposed distally of the mounting ring; and
(f) one or more electrical conduits coupling the drum with the piezoelectric components, wherein the electrical conduits are routed over or through the mounting ring, wherein the drum, the mounting ring, and the transducer comprise a unitarily rotatable assembly that is rotatable relative to the handle assembly.

* * * * *